United States Patent
Shi et al.

(10) Patent No.: US 10,646,518 B2
(45) Date of Patent: May 12, 2020

(54) APOPTOTIC BODIES

(71) Applicants: Alfred E. Mann Institute for Biomedical Engineering at the University of Southern California, Los Angeles, CA (US); University of Southern California, Los Angeles, CA (US)

(72) Inventors: Songtao Shi, Thousand Oaks, CA (US); Dawei Liu, Philadelphia, PA (US); Cunye Qu, Alhambra, CA (US)

(73) Assignees: ALFRED E. MANN INSTITUTE FOR BIOMEDICAL ENGINEERING AT THE UNIVERSITY OF SOUTHERN CALIFORNIA, Los Angeles, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 45 days.

(21) Appl. No.: 15/500,726

(22) PCT Filed: Aug. 7, 2015

(86) PCT No.: PCT/US2015/044308
§ 371 (c)(1),
(2) Date: Jan. 31, 2017

(87) PCT Pub. No.: WO2016/022972
PCT Pub. Date: Feb. 11, 2016

(65) Prior Publication Data
US 2017/0216364 A1   Aug. 3, 2017

Related U.S. Application Data

(60) Provisional application No. 62/035,246, filed on Aug. 8, 2014.

(51) Int. Cl.
*A61K 35/28* (2015.01)
*C12N 5/0775* (2010.01)
(Continued)

(52) U.S. Cl.
CPC ............ *A61K 35/28* (2013.01); *A61K 9/0053* (2013.01); *A61K 35/12* (2013.01); *C12N 5/0663* (2013.01)

(58) Field of Classification Search
CPC .............. A61K 2300/00; A61K 35/761; A61K 38/177; A61K 38/1891; A61K 38/50; A61K 45/06; A61K 31/5377; A61K 38/00; A61K 31/4025; A61K 31/4155; A61K 31/427; A61K 31/4439; A61K 31/513; A61K 48/005; A61K 48/00; A61K 31/444; A61K 31/497; A61K 31/506; A61K 31/721; A61K 31/4985; A61K 2039/505; A61K 2039/5158; A61K 2039/55505; A61K 2039/55566; A61K 35/28; A61K 38/17; A61K 38/61; A61K 39/0011; A61K 39/0225; A61K 39/61; A61K 38/1825; A61K 38/1866; A61K 31/437; A61K 35/12; A61K 39/39591; A61K 47/6843; A61K 51/1018; A61K 9/0019; A61K 9/0053; A61K 9/146; A61K 35/51; A61K 2039/6006; A61K 31/00; A61K 33/24; C07D 401/04; C07D 401/14; C07D 403/10; C07D 405/14; C07D 409/14; C07D 417/14; C07D 471/04; C07D 487/04; C07D 413/14; C07D 417/10; C07D 487/10; C07D 401/12; C07D 209/08; C07D 209/10; C07D 209/12; C07D 209/14; C07D 209/18; C07D 231/56; C07D 403/04; C07D 403/14; C07D 405/04; C07D 409/04; C07D 409/12; C07D 413/04; C07D 417/12; C07D 519/00; C07D 498/04; C07K 14/005; C07K 14/78; C07K 14/47; C07K 14/4702; C07K 2319/00; C07K 16/18; C07K 16/244;
(Continued)

(56) References Cited

U.S. PATENT DOCUMENTS 7,123,968 B1 * 10/2006 Casscells, III ....... A61N 5/0601
607/98
2001/0041342 A1 * 11/2001 Miller .................. C12N 5/0659
435/6.13
(Continued)

FOREIGN PATENT DOCUMENTS

FR        2980710        * 4/2013  ............ A61K 35/28
WO    2014/210037 A2    12/2014
WO    2015/038665 A1     3/2015

OTHER PUBLICATIONS

Maddens Stephane, FR2980710 English Abstract Only, Apr. 2013.*
(Continued)

*Primary Examiner* — Deborah K Ware
(74) *Attorney, Agent, or Firm* — Knobbe, Martens, Olson & Bear LLP

(57) ABSTRACT

This disclosure relates to apoptotic bodies. The disclosure particularly relates to a composition comprising the apoptotic bodies. The disclosure further relates to preparation of apoptotic bodies from stem cells. The disclosure also relates to medical treatments comprising the use of the composition comprising the apoptotic bodies. The apoptotic bodies may comprise apoptotic stem cells. The apoptosis of a cell may be induced by a starvation method, an ultra-violet irradiation method, a thermal stress method, a staurosporine method, or a combination thereof.

28 Claims, 34 Drawing Sheets

(51) Int. Cl.
*A61K 35/12* (2015.01)
*A61K 9/00* (2006.01)

(58) Field of Classification Search
CPC .......... C07K 2317/56; C07K 2317/565; C07K 14/435; C07K 14/575; C07K 16/00; C07K 2317/565101; C07K 2710/10032; C12N 15/86; C12N 15/1137; C12N 2310/14; C12N 2310/531; C12N 2710/16122; C12N 2710/16222; C12N 5/06; C12N 5/0663; C12N 9/00; C12N 9/64; C12N 2710/10345; C12N 7/00; C12N 2799/026; C12N 9/6489; C12N 5/0662; C12N 2710/10032; C12N 2710/10043; C12N 2710/10322; C12N 2710/10343; C12Y 305/04001; C12Y 204/0203; C07H 21/04; A61N 2005/063; A61N 2005/0645; A61N 2005/0659; A61N 2005/067; A61N 5/0618; A61N 5/10; B82Y 5/00; C12P 21/02; C12Q 1/68; C12Q 1/6886; C12Q 2600/106; C12Q 2600/118; C12Q 2600/156; C12Q 2600/158; C12Q 2600/15; G01N 2333/4703; G01N 2510/00; G01N 2800/52; G01N 2800/56; G01N 33/5017; G01N 33/574; G01N 33/57488; G01N 33/6875; G01N 2800/24; G01N 2800/245; G01N 33/56966; G01N 33/88; G01N 33/9493; Y10S 977/773; Y10S 977/915

See application file for complete search history.

(56) References Cited

U.S. PATENT DOCUMENTS

| | | | |
|---|---|---|---|
| 2005/0202098 A1* | 9/2005 | Mevorach | A61K 35/15 424/533 |
| 2006/0127383 A1* | 6/2006 | Hamet | A61M 1/3681 424/93.72 |
| 2011/0262392 A1* | 10/2011 | Habib | A61K 35/12 424/85.2 |
| 2012/0128636 A1 | 5/2012 | Le et al. | |
| 2013/0330300 A1 | 12/2013 | Shi et al. | |
| 2014/0154220 A1 | 6/2014 | Shi et al. | |
| 2015/0104428 A1 | 4/2015 | Shi et al. | |

OTHER PUBLICATIONS

Aggarwal et al. "Human mesenchymal stem cells modulate allogeneic immune cell responses" (2005) Blood 105:1815-1822.
Akiyama et al. "Mesenchymal-stem-cell-induced immunoregulation involves FAS-ligand-/FAS-mediated T cell apoptosis" (2012) Cell Stem Cell 10:544-555.
Atsuta et al. "Mesenchymal stem cells inhibit multiple myeloma cells via the Fas/Fas ligand pathway" Stem Cell Research & Therapy, 2013, 4:111.
Berda-Haddad et al., "Sterile inflamation of endothelial cell-derived apoptotic bodies is mediated by interleukin-1?," PNAS, Dec. 20, 2011, vol. 108, No. 51, pp. 20684-20689 and 2 pages of supporting information.
Egusa et al. "Stem Cells in Dentistry—Part I: Stem Cell Sources" J. Prosthodontic Res. (212) v56, p. 151-165.
Grau et al., "Apoptotic Cells Induce NF-kB and Inflammasome Negative Signaling," PLOS One, Mar. 30, 2015, 17 pages.
Hristov et al., "Apoptotic bodies from endothelial cells enhance the number and initiate the differentiation of human endothelial progenitor cells in vitro," Blood, Nov. 1, 2004, vol. 104, No. 9, pp. 2761-2766.
Le Blanc et al. "Mesenchymal stem cells for treatment of steroid-resistant, severe, acute graft-versus-host disease: a phase II study" (2008) Lancet 371:1579-1586.
Nauta et al. "Immunomodulatory properties of mesenchymal stromal cells" (2007) Blood 110:3499-3506.
Perruche et al., "AB0120 Apoptotic Cell-Based Therapy to Treat Collagen-Induced Experimental Arthritis. Rationale for the Use of Apoptotic Cells in the Treatment of Rheumatoid Arthritis," Eular Scientific Abstracts, 2014, 3 pages.
Sun et al. "Mesenchymal stem cell transplantation reverses multiorgan dysfunction in systemic lupus erythematosus mice and humans" (2009) Stem Cells 27:1421-1432.
Uccelli et al. "Mesenchymal stem cells in health and disease" (2008) Nat. Rev. Immunol. 8:726-736.
Wonnacott K. "Cellular Therapy Products" Food and Drug Administration, Web Seminar Series, UCM273197, retrieved from https://www.fda.gov/downloads/BiologicsBloodVaccines/InternationalActivities/UCM273197.pdf.
Zernecke et al., "Delivery of MicroRNA-126 by Apoptotic Bodies Induces CXCL12-Dependent Vsascular Protection," Dec. 8, 2009, Science Signaling, vol. 2, issue 100, ra81, 11 pages.
Pei-Hsun Sung et al., "Apoptotic adipose-derived mesenchymal stem cell therapy protects against lung and kidney injury in sepsis syndrome caused by cecal ligation puncture in rats." Stem Cell Research & Therapy, Biomed Central Ltd, London, UK, vol. 4, No. 6, Dec. 25, 2013 (Dec. 25, 2013), p. 155.
Chia-Lo Chang et al., "Impact of apoptotic adipose-derived mesenchymal stem cells on attenuating organ damage and reducing mortality in Rat sepsis syndrome induced by cecal puncture and ligation." Journal of Translational Medicine, Biomed Central, vol. 10, No. 1, Dec. 7, 2012 (Dec. 7, 2012), p. 244.
Thum Thomas et al., "The Dying Stem Cell Hypothesis Immune Modulation as a Novel Mechanism for Progenitor Cell Therapy in Cardiac Muscle.", Journal of the American College of Cardiology, vol. 46, No. 10, pp. 1799-1802.
Saas Philippe et al., "Prospects of apoptotic cell-based therapies for transplantation and inflammatory diseases." Immunotherapy, vol. 5, No. 10, Oct. 2013 (Oct. 2013), pp. 1055-1073.
Extended European Search Report issued by the EPO dated Dec. 15, 2017 for Application No. 15830332.1.

* cited by examiner

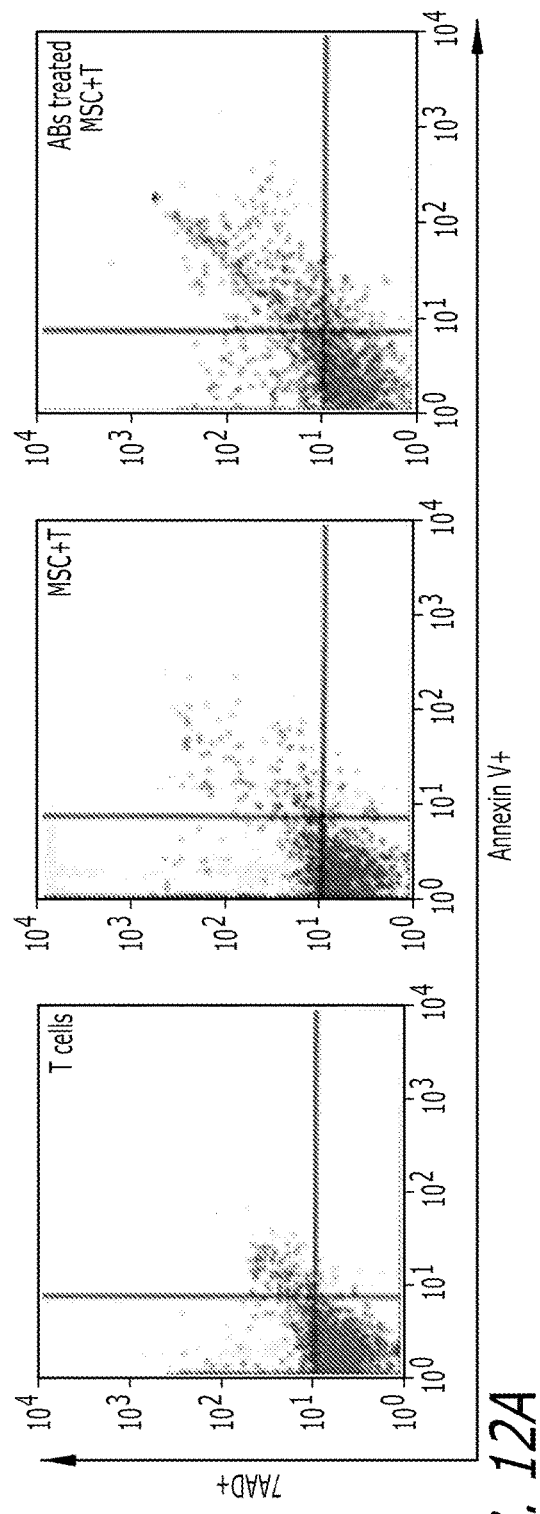
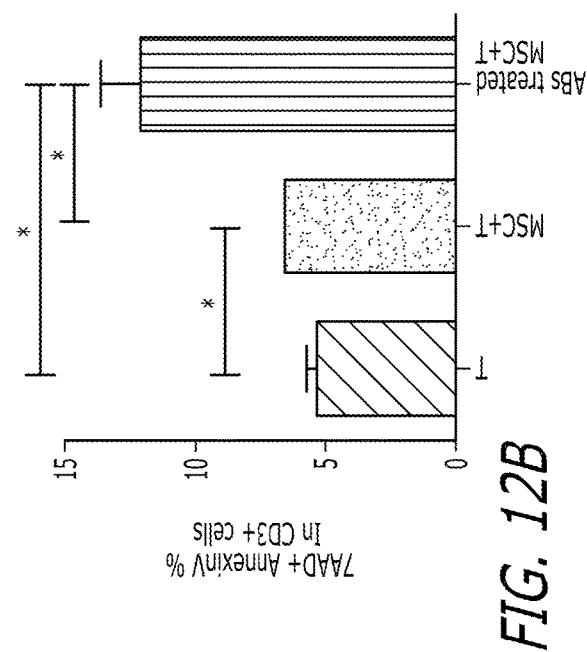
FIG. 12A
FIG. 12B

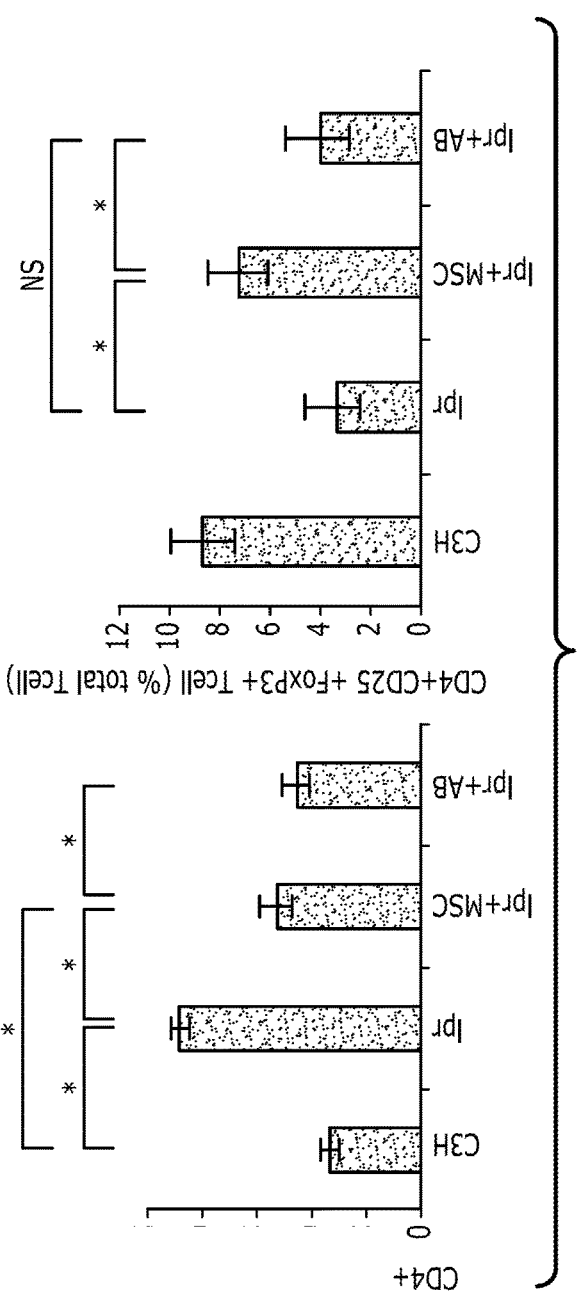
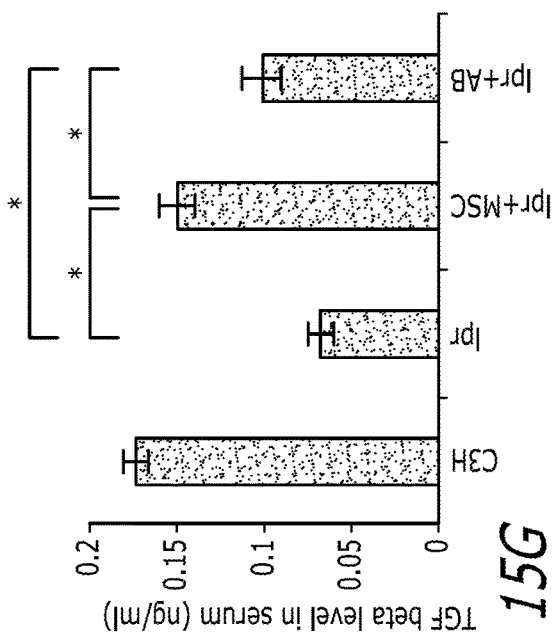
FIG. 15F
FIG. 15G

APOPTOTIC BODIES

CROSS-REFERENCE TO RELATED APPLICATION

This application is a United States national phase application under 35 U.S.C. 371 of International Application No. PCT/US2015/044308, filed on Aug. 7, 2015, which is based upon and claims the benefit of U.S. provisional patent application No. 62/035,246, entitled "Apoptotic Bodies," filed Aug. 8, 2014, the entire content of which are incorporated herein by reference.

TECHNICAL FIELD

This disclosure relates to apoptotic bodies. The disclosure particularly relates to a composition comprising the apoptotic bodies. The disclosure further relates to preparation of apoptotic bodies from stem cells. The disclosure also relates to medical treatments comprising the use of the composition comprising the apoptotic bodies.

DESCRIPTION OF RELATED ART

This disclosure generally relates to cell therapies and cell therapy products. Some examples of cell therapy products include stem cell derived products and stem cells, such as those from mesenchymal, hematopoietic, embryonic, and umbilical cord blood; cancer therapies and immunotherapies, such as dendritic cell vaccines; activated T or B lymphocytes, monocytes, and modified or unmodified cancer cells, allogeneic pancreatic islet cells, bone-forming cells for bone regeneration, chondrocytes for cartilage repair, keratinocytes, fibroblasts, and hepatocytes. See, for example, Wonnacott K. "Cellular Therapy Products" Food and Drug Administration, Web Seminar Series, UCM273197. The entire content of this publication is incorporated herein by reference.

An example of a cell therapy product is a composition comprising mesenchymal stem cells (MSCs). The MSCs possess multipotent differentiation potential and capability to regulate immune response. For example, see Uccelli et al. "Mesenchymal stem cells in health and disease" (2008) Nat. Rev. Immunol. 8:726-736; Nauta et al. "Immunomodulatory properties of mesenchymal stromal cells" (2007) Blood 110:3499-3506; and Aggarwal et al. "Human mesenchymal stem cells modulate allogeneic immune cell responses" (2005) Blood 105:1815-1822; the entire content of these publications is incorporated herein by reference. Cell types that MSCs have been shown to differentiate into in vitro or in vivo include osteoblasts, chondrocytes, myocytes, adipocytes, endotheliums, and beta-pancreatic islets supporting cells.

MSCs have a large capacity for self-renewal while maintaining their multipotency. The standard test to confirm multipotency is differentiation of the cells into osteoblasts, adipocytes, and chondrocytes and possibly neuron-like cells. However, the degree to which the culture will differentiate varies among individuals and how differentiation is induced, e.g. chemical vs. mechanical. The capacity of cells to proliferate and differentiate is known to decrease with the age of the donor, as well as the time in culture.

It was disclosed that human MSCs may avoid allorecognition, interfere with dendritic cell and T-cell function and generate a local immunosuppressive microenvironment by secreting cytokines. It was also disclosed that the immunomodulatory function of human MSCs may be enhanced when the cells are exposed to an inflammatory environment characterized by the presence of elevated local interferon-gamma levels.

Thus, MSCs may be used in tissue regeneration and immune therapies. For example, see Le Blanc et al. "Mesenchymal stem cells for treatment of steroid-resistant, severe, acute graft-versus-host disease: a phase II study" (2008) Lancet 371:1579-1586; Sun et al. "Mesenchymal stem cell transplantation reverses multiorgan dysfunction in systemic lupus erythematosus mice and humans" (2009) Stem Cells 27:1421-1432; and Akiyama et al. "Mesenchymal-stem-cell-induced immunoregulation involves FAS-ligand-/FAS-mediated T cell apoptosis" (2012) Cell Stem Cell 10:544-555; the entire content of these publications is incorporated herein by reference.

However, there still exists a need for other sources of cell therapy products and new approaches for preparation thereof, and use of such products for medical treatments.

SUMMARY

This disclosure relates to apoptotic bodies. The disclosure particularly relates to a composition comprising the apoptotic bodies. The disclosure further relates to preparation of apoptotic bodies from stem cells. Preferably, the apoptotic bodies are prepared from multipotent or pluripotent stem cells, and not from totipotent stem cells. More preferably, the apoptotic bodies are prepared from multipotent stem cells, and not from pluripotent or totipotent stem cells. The disclosure also relates to medical treatments comprising the use of the composition comprising the apoptotic bodies.

This disclosure relates to a composition. This composition may be suitable for a treatment of a mammal. This composition may comprise an apoptotic body. The apoptotic body may comprise a apoptotic stem cell.

In this disclosure, the apoptotic stem cell may comprise any apoptotic stem cell. For example, the apoptotic stem cell may comprise an apoptotic mesenchymal stem cell, an apoptotic embryonic stem cell, an apoptotic fetal stem cell, an apoptotic adult stem cell, an apoptotic amniotic stem cell, an apoptotic cord blood stem cell, an apoptotic induced pluripotent stem cell, or a combination thereof. For example, the apoptotic stem cell may comprise an apoptotic mesenchymal stem cell. For example, the apoptotic stem cell may comprise an apoptotic bone marrow-derived mesenchymal stem cell, an apoptotic dental pulp stem cell, an apoptotic stem cell from human exfoliated deciduous teeth, an apoptotic periodontal ligament stem cell, an apoptotic dental follicle stem cell, an apoptotic tooth germ progenitor cell, an apoptotic stem cell from the apical papilla, an apoptotic oral epithelial progenitor/stem cell, an apoptotic gingiva-derived mesenchymal stem cell, an apoptotic periosteum-derived stem cell, an apoptotic salivary gland-derived stem cell, or a combination thereof. For example, the apoptotic stem cell may comprise an apoptotic body derived from cultured mesenchymal stem cell, an apoptotic body derived from an uncultured gingiva-derived mesenchymal stem cell, an apoptotic dental pulp stem cell, an apoptotic bone-marrow-derived stem cell, or a combination thereof.

In this disclosure, the apoptotic stem cell may be obtained by the apoptosis of a stem cell, For example, the apoptosis of a stem cell may be induced by a starvation method, an ultra-violet irradiation method, a thermal stress method, a staurosporine method, or a combination thereof.

For example, the apoptotic stem cell may be obtained by incubating a stem cell in a serum-free medium for a time period in the range of 1 hour to 1,000 hours. Or, the apoptotic stem cell may be obtained by incubating a stem cell in a serum-free medium for a time period in the range of 10 hours to 100 hours.

In another example, the apoptotic stem cell may be obtained by heating a stem cell at a temperature in the range of 30° C. to 100° C. for a predetermined period of time. Or, the apoptotic stem cell may be obtained by heating a stem cell at a temperature in the range of 30° C. to 100° C. for a time period in the range of 1 minute to 1,000 minutes. Or, the apoptotic stem cell may be obtained by heating a stem cell at a temperature in the range of 30° C. to 100° C. for a time period in the range of 10 minutes to 100 minutes. Or, the apoptotic stem cell may be obtained by heating a stem cell at a temperature in the range of 40° C. to 70° C. for a predetermined time. Or, the apoptotic stem cell may be obtained by heating a stem cell at a temperature in the range of 40° C. to 70° C. for a time period in the range of 1 minute to 1,000 minutes. Or, the apoptotic stem cell may be obtained by heating a stem cell at a temperature in the range of 40° C. to 70° C. for a time period in the range of 10 minute to 100 minutes.

Yet, in another example, the apoptotic stem cell may be obtained by treating a stem cell with staurosporine in an amount in the range of 1 nm staurosporine to 10,000 nM staurosporine for a time period in the range 1 hour to 1,000 hours. Or, the apoptotic stem cell may be obtained by treating a stem cell with staurosporine in an amount in the range of 1 nm staurosporine to 10,000 nM staurosporine for a time period in the range 5 hours to 100 hours. Or, the apoptotic stem cell may be obtained by treating a stem cell with staurosporine in an amount in the range of 100 nm staurosporine to 1,000 nM staurosporine for a time period in the range 1 hour to 1,000 hours. Or, the apoptotic stem cell may be obtained by treating a stem cell with staurosporine in an amount in the range of 100 nm staurosporine to 1,000 nM staurosporine for a time period in the range 5 hours to 100 hours. Or, the apoptotic stem cell may be obtained by treating a stem cell in a serum free medium with staurosporine in an amount in the range of 1 nm staurosporine to 10,000 nM staurosporine for a time period in the range of 1 hour to 1,000 hours. Or, the apoptotic stem cell may be obtained by treating a stem cell in a serum free medium with staurosporine in an amount in the range of 1 nm staurosporine to 10,000 nM staurosporine for a time period in the range of 5 hours to 100 hours. Or, the apoptotic stem cell may be obtained by treating a stem cell in a serum free medium with staurosporine in an amount in the range of 100 nm staurosporine to 1,000 nM staurosporine for a time period in the range of 1 hour to 1,000 hours. Or, the apoptotic stem cell may be obtained by treating a stem cell in a serum free medium with staurosporine in an amount in the range of 100 nm staurosporine to 1,000 nM staurosporine for a time period in the range of 5 hours to 100 hours.

Yet, in another example, the apoptotic stem cell may be obtained by irradiating a stem cell at a wavelength in the range of 100 nm to 400 nm for a time period in the range of 0.1 minute to 1,000 minutes. Or, the apoptotic stem cell may be obtained by irradiating a stem cell at a wavelength in range of 100 nm to 400 nm for a UV lamp for a time period in the range of 1 minute to 100 minutes.

This disclosure also relates to a method for preparation of the composition of this disclosure. This preparation method may, for example, comprise inducing apoptosis of a stem cell and thereby preparing the apoptotic body comprising the apoptotic stem cell.

In this preparation method, the stem cell may comprise any stem cell. For example, the stem cell may comprise an embryonic stem cell, a fetal stem cell, an adult stem cell, an amniotic stem cell, a cord blood stem cell, an induced pluripotent stem cell, or a combination thereof. For example, the stem cell may comprise a mesenchymal stem cell. For example, the stem cell may comprise a bone marrow-derived mesenchymal cell, a dental pulp stem cell, a stem cell from human exfoliated deciduous teeth, a periodontal ligament stem cell, a dental follicle stem cell, a tooth germ progenitor cell, a stem cell from the apical papilla, an oral epithelial progenitor/stem cell, a gingiva-derived mesenchymal stem cell, a periosteum-derived stem cell, a salivary gland-derived stem cell, or a combination thereof. For example, the stem cell may comprise a cultured mesenchymal stem cell, an uncultured gingiva-derived mesenchymal stem cell, a dental pulp stem cell, a bone-marrow-derived stem cell, or a combination thereof.

For example, in this disclosure, the apoptosis may be induced by a starvation method, an ultra-violet irradiation method, a thermal stress method, a staurosporine method, or a combination thereof.

In this disclosure, the apoptotic body may, for example, be collected the by centrifugation.

The preparation method may further comprise identifying, quantifying, and/or isolating the apoptotic body by a fluorescent microscopy technique, a flow cytometry technique, a centrifugation technique, or a combination thereof.

This disclosure also relates to a method of treating a human subject. This treatment method may, for example, comprise administrating an effective amount of a composition, comprising an apoptotic body comprising an apoptotic stem cell of a human, into the human subject and thereby treating the human subject.

In this disclosure, the treating may comprise treating a disease. The disease may, for example, may comprise an inflammatory, an autoimmune disease, bone loss caused by ovariectomy, a tumor formation and/or a wound.

For example, the inflammatory and/or autoimmune disease may be graft-versus host disease (GvHD), diabetes, rheumatoid arthritis (RA), autoimmune encephalomyelitis, systemic lupus erythematosus (SLE), multiple sclerosis (MS), periodontitis, inflammatory bowel disease (IBD), mucositis, colitis, sepsis, the like, or a combination thereof. For example, the inflammatory and/or autoimmune disease may comprise colitis. For example, the inflammatory and/or autoimmune disease may comprise systemic lupus erythematosus. For example, the disease may be bone loss caused by ovariectomy. For example, the disease may be a tumor formation. For example, the tumor may be hepatocellular carcinoma, multiple myeloma, or a combination thereof. For example, the disease may be a wound.

In the treatment method, the apoptotic stem cell of a human may, for example, comprise an apoptotic mesenchymal stem cell of a human, an apoptotic embryonic stem cell of a human, an apoptotic fetal stem cell of a human, an apoptotic adult stem cell of a human, an apoptotic amniotic stem cell of a human, an apoptotic cord blood stem cell of a human, an apoptotic induced pluripotent stem cell of a human, or a combination thereof. For example, the apoptotic stem cell of a human may comprise an apoptotic mesenchymal stem cell of a human. For example, the apoptotic stem cell of a human may comprise an apoptotic bone marrow-derived mesenchymal cell of a human, an apoptotic dental pulp stem cell of a human, an apoptotic stem cell from human exfoliated deciduous teeth of a human, an apoptotic periodontal ligament stem cell of a human, an apoptotic dental follicle stem cell of a human, an apoptotic tooth germ progenitor cell of a human, an apoptotic stem cell from the apical papilla of a human, an apoptotic oral epithelial progenitor/stem cell of a human, an apoptotic gingiva-derived mesenchymal stem cell of a human, an apoptotic periosteum-derived stem cell of a human, an apoptotic salivary gland-derived stem cell of a human, or a combination thereof. For example, the apoptotic stem cell of a human may comprise an apoptotic body derived from cultured mesenchymal stem cell of a human, an apoptotic body derived from an uncultured gingiva-derived mesenchymal stem cell of a human, an apoptotic dental pulp stem cell of a human, an apoptotic bone-marrow-derived stem cell of a human, or a combination thereof.

This disclosure also relates to a method of improvement of stem cell properties ("improvement method"). The improvement method may comprise using an effective amount of a composition of this disclosure. The improvement method may comprise an apoptotic body comprising an apoptotic stem cell. The improvement method may improve: (a) colony formation of bone marrow mesenchymal stem cells in vivo and/or in vitro; (b) immunomodulation of bone marrow mesenchymal stem cells in vivo and/or in vitro; (c) osteogenesis of bone marrow mesenchymal stem cells in vivo and/or in vitro; (d) adipogenesis of bone marrow mesenchymal stem cells in vivo and/or in vitro; or a combination thereof. For example, the improvement method may comprise improving the colony formation of bone marrow mesenchymal stem cells in vivo and/or in vitro. For example, the improvement method may comprise improving the immunomodulation of bone marrow mesenchymal stem cells in vivo and/or in vitro. For example, the improvement method may comprise improving the osteogenesis of bone marrow mesenchymal stem cells in vivo and/or in vitro. For example, the improvement method may comprise improving the adipogenesis of bone marrow mesenchymal stem cells in vivo and/or in vitro.

Any combination of products such as compositions comprising apoptotic bodies, methods of their preparation, and methods of their use that are described herein may also be made and followed.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

FIGS. 12A-B. Improvement of immunomodulation potential of BMMSCs in vitro by apoptotic body treatment.

FIGS. 15A-G. Treatment of the systemic lupus erythematosus (SLE) mice with apoptotic bodies.

DETAILED DESCRIPTION OF ILLUSTRATIVE EMBODIMENTS

Figure 1:
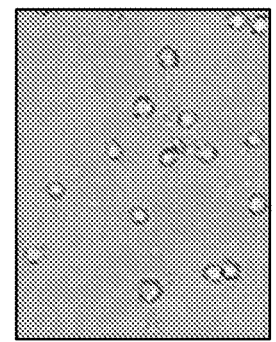
FIG. 1. Schematic demonstration of GMSCs. The cell apoptosis was induced by the staurosporine method. The cell apoptosis was detected by using the light microscope and the flow cytometric analysis.
Figure 1:
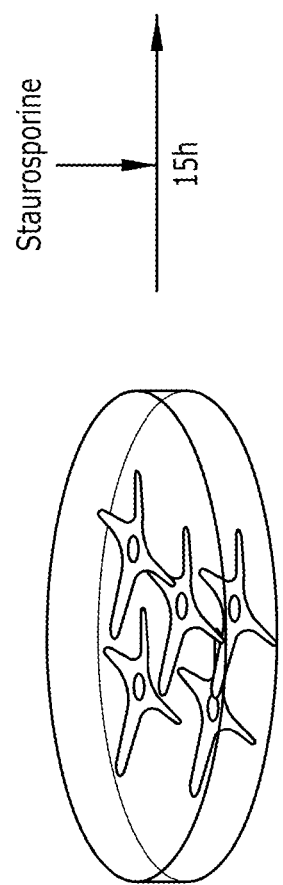
Figure 1:
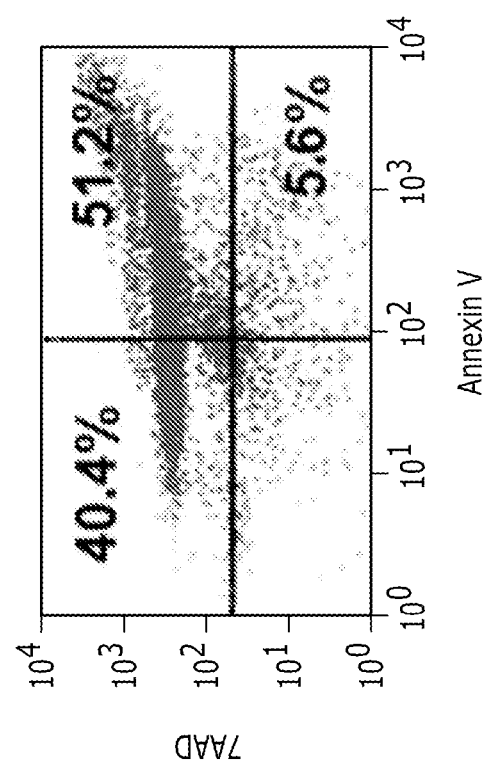
Figure 1:
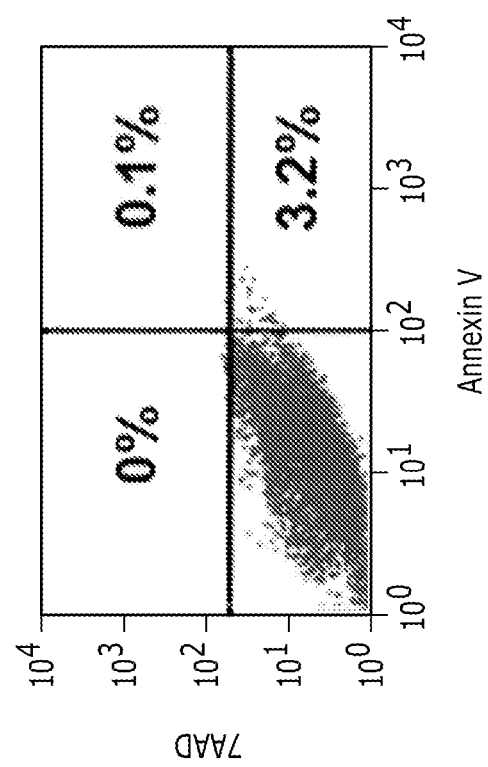

Illustrative embodiments are now discussed. Other embodiments may be used in addition or instead. Certain details which may be apparent to a person of ordinary skill in the art or unnecessary may have been omitted from this disclosure to to provide for a clear and concise disclosure. Conversely, some embodiments may be practiced without all of the details which are disclosed.

The following acronyms and abbreviations were used in this disclosure.

AB: Apoptotic Bodies
BMMSC: Bone-Marrow-derived Mesenchymal Stem Cell
BMD: Bone Mineral Density
CFU-F: Colony Forming Unit-Fibroblast
DFSC: Dental Follicle Stem Cell
DPSC: Dental Pulp Stem Cell
DSS: Dextran Sulfate Sodium
FACS: Fluorescence Assisted Cell Sorting
GMSC: Gingiva-derived Mesenchymal Stem Cell
GvHD: Graft-versus-Host Disease
HE: Hematoxylin and Eosin
HA/TCP: Hydroxyapatite Tricalcium Phosphate
MSC: Mesenchymal Stem Cell
nM: nano-Molar
OESC: Oral Epithelial Progenitor/Stem Cell
PDLSC: Periodontal Ligament Stem Cell
PSC: Periosteum-derived Stem cell
SCAP: Stem Cells from the Apical Papilla
SGSC: Salivary Gland-derived Stem Cell
SHED: Stem Cell from Human Exfoliated Deciduous Teeth
SLE: Systemic Lupus Erythematosus
TGPC: Tooth Germ Progenitor Cell
UV: Ultra-Violet
μm: micrometer This disclosure relates to apoptotic bodies. The disclosure particularly relates to a composition comprising the apoptotic bodies. The disclosure further relates to preparation of apoptotic bodies from stem cells. The disclosure also relates to medical treatments comprising using the composition comprising the apoptotic bodies.

Apoptotic bodies may be vesicles that are approximately 0.5-10 μm in diameter and generated by cells undergoing programmed cell death, termed apoptosis, which may initiate with cell shrinkage and condensation of the nuclear chromatin, followed by membrane blebbing. Cellular organelles, condensed chromatin and their fragmentations may be encapsulated into the plasma membrane to form apoptotic bodies. Apoptotic bodies may be collected from apoptotic cells by series centrifuge, as disclosed in Example 3. Apoptotic bodies may be characterized as phosphatidylserine exposure on the surface membrane that may be detected with Annexin V staining and other surface marker, such as TSP-1. About 10% apoptotic bodies may contain genetic material that may be labeled with Hoechst 33342.

This disclosure also relates to an apoptotic body therapy (or apoptotic body treatment). The apoptotic body treatment may include, but not limited to, diagnosis, treatment, cure, healing, mitigation, or prevention of a disease or injury in, and/or cosmetic treatment of a mammal. The mammal may be a human. The mammal may be a non-human animal, such as a non-human primate, a horse, a sheep, a cattle, a hog, a dog, a cat, and a goat.

This disclosure further relates to methods of using the composition comprising apoptotic bodies in the treatment of tumors, and inflammatory and/or autoimmune diseases ("treatment methods"). Examples of the tumors may be hepatocellular carcinoma and multiple myeloma. Examples of such diseases are graft-versus-host disease (GvHD), diabetes, rheumatoid arthritis (RA), autoimmune encephalomyelitis, systemic lupus erythematosus (SLE), multiple sclerosis (MS), periodontitis, inflammatory bowel disease (IBD), alimentary tract mucositis induced by chemo- or radiotherapy, colitis, and sepsis. Another example of the treatment method may be the treatment of the bone loss caused by ovariectomy.

This disclosure also relates to of using the composition comprising apoptotic bodies in the improvement of BMMSCs ("improvement methods"). Examples of such uses to improve BMMSCs include use for the improvement of colony formation of bone marrow mesenchymal stem cells in vivo or in vitro, improvement of osteogenesis of bone marrow mesenchymal stem cells in vivo or in vitro, improvement of adipogenesis of bone marrow mesenchymal stem cells in vivo or in vitro, improvement of immunomodulation of bone marrow mesenchymal stem cells in vivo or in vitro, and combinations thereof.

The composition useful for a treatment may comprise an apoptotic body. The composition may comprise and apoptotic body that may be prepared by apoptosis of a stem cell. In one example, the apoptotic body may comprise an apoptotic stem cell. The apoptotic stem cell may be a stem cell prepared by apoptosis a stem cell. In all embodiments of this disclosure, it is preferred that the apoptotic bodies are prepared from multipotent or pluripotent stem cells, and not from totipotent stem cells. More preferably, the apoptotic bodies are prepared from multipotent stem cells, and not from pluripotent or totipotent stem cells.

In this disclosure, the stem cell may be a stem cell of a mammal. The mammal may be a human. The mammal may be a non-human animal, such as a non-human primate, a horse, a sheep, a cattle, a hog, a dog, a cat, and a goat.

In this disclosure, the stem cell of a human may be used to prepare an apoptotic stem cell. Such human derived apoptotic stem cells may be used in treatment of human subjects.

This disclosure relates to a composition. The composition may comprise an apoptotic body. The composition may comprise a cell culture comprising an apoptotic body. The composition may be a drug or a biologic formulation. The composition may be used in the apoptotic body treatment.

In this disclosure, the composition may comprise an apoptotic body comprising apoptotic stem cells.

Stem cells, which are suitable for preparation of the exemplary composition, may be any stem cell of any mammal. For example, the stem cells may be stem cells of a mammal that undergoes the treatment (i.e. apoptotic body treatment comprising using apoptotic bodies comprising apoptotic autologous stem cells, "autologous apoptotic body treatment"). Or, the stem cells may be stem cells of a mammal other than the mammal that undergoes the treatment (i.e. allogeneic body treatment comprising using apoptotic bodies comprising apoptotic allogeneic stem cells, "allogeneic apoptotic body treatment").

Following are examples of the stem cells that are suitable in preparation of the apoptotic bodies comprising apoptotic stem cells.

The stem cell may be any stem cell. Examples of stem cells may be embryonic stem cells, fetal stem cells, adult stem cells, amniotic stem cells, cord blood stem cells, induced pluripotent stem cells, or combinations thereof.

An example of stem cells may comprise mesenchymal stem cells (MSCs). Examples of mesenchymal stem cells may comprise bone marrow-derived mesenchymal cells (BMMSCs), dental pulp stem cells (DPSCs), stem cells from human exfoliated deciduous teeth (SHED), periodontal ligament stem cells (PDLSCs), dental follicle stem cells (DFSCs), tooth germ progenitor cells (TGPCs), stem cells from the apical papilla (SCAPs), oral epithelial progenitor/stem cells (OESCs), gingiva-derived mesenchymal stem cells (GMSCs), periosteum-derived stem cells (PSCs), salivary gland-derived stem cells (SGSCs), and combinations thereof.

For in detail disclosure of such stem cells, tissues suitable for their harvest, methods of their isolation from such tissues, their expansion, and methods of administration of such stem cells for a treatment, see, for example, Egusa et al. "Stem Cells in Dentistry—Part I: Stem Cell Sources" J. Prosthodontic Res. (212) v56, p 151-165; Shi et al. "A composition of stem cells having highly expressed Fas ligand," WO2015038665A1; Atsuta et al. "Mesenchymal stem cells inhibit multiple myeloma cells via the Fas/Fas ligand pathway" Stem Cell Research & Therapy, 2013, 4:111; Le et al. "Gingiva Derived Stem Cell and Its Application in Immunomodulation and Reconstruction", U.S. 2012/0128636A1; Shi et al. "A Composition of Mesenchymal Stem Cells", WO2014210037; Shi et al. "Compositions and Treatment Methods for Mesenchymal Stem Cell-Induced Immunoregulation," US20150104428 A1; Shi et al. "High Telomerase Activity Bone Marrow Mesenchymal Stem Cells, Methods of Producing the Same and Pharmaceuticals and Treatment Methods Based Thereon," US20130330300 A1; and Shi et al. "Methods and Compositions for Improved Tissue Regeneration by Suppression of Interferon-Gamma and Tumor Necrosis Factor-Alpha," US20140154220 A1. The entire content of each of these publications is incorporated herein by reference.

In another example, cultured and/or uncultured MSCs may be used in preparation of apoptotic bodies. In another example, uncultured and/or GMSCs, DPSCs or a combination thereof may be used. Yet, in another example, cultured and/or uncultured BMMSCs may be used. Still, in another example, a combination of these uncultured and/or cultured stem cells may be used.

The apoptotic stem cells may thereby be prepared from the stem cells. Thus, examples of such apoptotic stem cells may be an apoptotic mesenchymal stem cell, an apoptotic embryonic stem cell, an apoptotic fetal stem cell, an apoptotic adult stem cell, an apoptotic amniotic stem cell, an apoptotic cord blood stem cell, an apoptotic induced pluripotent stem cell, and a combination thereof. For example, the apoptotic stem cells may be a apoptotic bone marrow-derived mesenchymal cell, an apoptotic dental pulp stem cell, an apoptotic stem cell from human exfoliated deciduous teeth, an apoptotic periodontal ligament stem cell, an apoptotic dental follicle stem cell, an apoptotic tooth germ progenitor cell, an apoptotic stem cell from the apical papilla, an apoptotic oral epithelial progenitor/stem cell, an apoptotic gingiva-derived mesenchymal stem cell, an apoptotic periosteum-derived stem cell, an apoptotic salivary gland-derived stem cell, or a combination thereof. In other examples, the apoptotic stem cell may comprise an apoptotic body derived from cultured mesenchymal stem cell, an apoptotic body derived from an uncultured gingiva-derived mesenchymal stem cell, an apoptotic dental pulp stem cell, an apoptotic bone-marrow-derived stem cell, or a combination thereof.

Apoptosis of the stem cells may be achieved by using variety of methods. For example, the apoptotic stem cell may be prepared by inducing apoptosis of the stem cell. The examples of the stem cells apoptosis method may include a stem cell starvation method, a ultra-violet irradiation method, a thermal stress method, a staurosporine method, and combinations thereof.

The cell apoptosis may be detected by using variety of methods. Examples of the detection methods may be the detection by using a light microscope, the detection by using flow cytometry, and combinations thereof.

The apoptotic bodies may be collected by centrifugation.

The apoptotic bodies may be identified, quantified, and and/or purified by a fluorescent microscopy technique, a flow cytometry technique, and/or a centrifugation technique.

This disclosure also relates to a method of preparation ("preparation method"). The preparation method may, for example, comprise obtaining (or harvesting) a tissue comprising stem cells, preparing an apoptotic body using the tissue comprising stem cells, and preparing a composition comprising an apoptotic body. In another example, the preparation method may comprise obtaining (or harvesting) a tissue comprising stem cells, separating the tissue into cells, sorting stem cells from the cells, preparing an apoptotic body using the sorted stem cells, and preparing a composition comprising the apoptotic body. Yet, in another example, the preparation method may comprise obtaining (or harvesting) a tissue comprising stem cells, separating the tissue into cells, sorting stem cells from the cells, expanding the stem cells, preparing an apoptotic body using the expanded stem cells, and preparing a composition comprising the apoptotic body. The preparation method may further comprise culturing the separated cells before sorting the stem cells. The preparation method may further comprise isolating a stem cell.

This disclosure also relates to a method of administration of the composition comprising apoptotic bodies ("administration method"). The administration method may comprise any method suitable for administration of a cell or a tissue. The composition comprising the apoptotic bodies suitable for the treatment purposes may be administered (or delivered) in various ways. For example, they may be infused, injected at various sites, or surgically implanted.

Suitable compositions include, for example, an apoptotic body (or cell) suspension in a liquid (preferably aqueous) medium, and apoptotic bodies in aggregated form with or without solid supports or encapsulating materials. The liquid medium may be a pharmaceutically acceptable liquid medium. The liquid medium may be suitable for injection. Suitable liquid media are generally well known and include, for example, normal saline (with or without glucose and/or potassium), Ringer's solution, Lactated Ringer's solution, and Hartmann's solution.

The composition may be administered in an amount effective to treat a mammal. The apoptotic body amount (or dose) of the composition may be an amount effective to treat a mammal. The amount and/or concentration of apoptotic bodies in the composition can be selected to provide for convenient administration of an amount (of the composition that is acceptable for the mammal being treated. For example, a liquid composition that contain a high concentration of apoptotic bodies is suitable for injection of a relatively small volume into solid tissue, while a liquid composition that contains a lower concentration of apoptotic bodies may be advantageous for administration by intravenous infusion. Suitable liquid compositions can contain, for example, about $1\times10^1$ apoptotic bodies/mL to about $1\times10^{10}$ apoptotic bodies/mL, or about $1\times10^5$ apoptotic bodies/mL to about $1\times10^7$ apoptotic bodies/mL, or about $1\times10^6$ apoptotic bodies/mL to $5\times10^6$ apoptotic bodies/mL. Aggregated or solid compositions can contain, for example, about $1\times10^1$ apoptotic bodies/mg to about $1\times10^{10}$ apoptotic bodies/g.

The composition may further comprise a carrier. The carrier may be suitable to host the apoptotic body. Example of the carrier may be in the form of matrices, tissues, fibers, beads, or other materials.

For therapeutic purposes, an effective amount of the composition may be administered to a mammal in need thereof. An "effective amount" in an amount that produces the desired effect under the conditions of administration, for example, an amount sufficient to inhibit inflammation, inhibit an immune or autoimmune response, inhibit bone loss, inhibit tumor growth or metastasis, promote wound healing, or promote colony formation, osteogenesis or adipogenesis by BMMSCs.

Generally, the effective amount may include about $1\times10^1$ apoptotic bodies to about $1\times10^{10}$ apoptotic bodies, or about $1\times10^5$ apoptotic bodies to about $1\times10^7$ apoptotic bodies, or about $1\times10^6$ apoptotic bodies to $5\times10^6$ apoptotic bodies per administration. The exact dosage of apoptotic cells to be administered may dependent upon a variety of factors, including the age, weight, and sex of the mammal, the disease being treated, and the extent and severity thereof. A clinician of ordinary skill can determine the appropriate dose and method for administration based on these and other considerations.

In this disclosure, the apoptotic stem cell may be obtained by the apoptosis of a stem cell induced by a starvation method, an ultra-violet irradiation method, a thermal stress method, a staurosporine method, or a combination thereof. These methods may be carried out in a serum free medium.

For example, to induce cell apoptosis by starvation method, the apoptotic stem cell may be obtained by incubating stem cell in a serum-free medium for a time period in the range of 1 hour to 1,000 hours, or in the range of 10 hours to 100 hours.

For example, to induce cell apoptosis by a thermal stress method, the apoptotic stem cell may be obtained by heating a stem cell at a predetermined temperature for a predetermined period of time. For example, to induce cell apoptosis by a thermal stress method, the apoptotic stem cell may be obtained by heating a stem cell at a temperature in the range of 30° C. to 100° C., or in the range of 40° C. to 70° C.; for a period of time in the range of 1 minute to 1,000 minutes, or 10 minutes to 100 minutes. The thermal stress method may be carried out in a serum free medium.

For example, to induce cell apoptosis by a staurosporine method, the apoptotic stem cell may be obtained by treating a stem cell with a predetermined amount of staurosporine for a predetermined period of time. For example, the apoptotic stem cell may be obtained by treating a stem cell with staurosporine in an amount in the range of 1 nm staurosporine to 10,000 nM staurosporine, or in an amount in the range of 1 nm staurosporine to 10,000 nM staurosporine; for a time period in the range 1 hour to 1,000 hours, or in the range 5 hours to 100 hours. The staurosporine method may be carried out in a serum free medium.

For example, to induce cell apoptosis by a ultra-violet (UV) method, a stem cell may be irradiated at a predetermined wavelength for a predetermined period of time. For example, the stem cell may be irradiated at a wavelength in the range of 100 nm to 400 nm for a time period in the range of 0.1 minute to 1,000 minutes, or in the range of 1 minute to 100 minutes. The UV radiation method may be carried out in a serum free medium.

Any combination of products such as compositions comprising apoptotic bodies, compositions comprising apoptotic bodies comprising apoptotic stem cells, methods of their preparation, and methods of their use that are described herein may also be made and followed.

Other examples of this disclosure are as follows.

Example 1. Procedure to Induce Cell Apoptosis

The cell apoptosis may be achieved by using variety of methods.

For example, in a starvation method, cells substantially comprising confluent MSCs were incubated in serum-free medium for about 72 hours to induce cell apoptosis. In this method, the cells may comprise close to 100% confluent MSCs.

In a UV irradiation method, i.e. another exemplary method, in, cultured MSCs may be treated with a UV lamp for a time period in the range of 5 minutes to 10 minutes to induce apoptosis The UV lamp may be operated at about 110 V, about 50 Hz, and about 180 W.

In a thermal stress method, i.e. another exemplary method, cultured MSCs may be incubated at a temperature varying in the range of 45° C. to 50° C. for a time period in the range of 40 minutes to 60 minutes to induce apoptosis.

In a staurosporine method, i.e. another exemplary method, cells substantially comprising confluent MSCs were treated with about 250 nM staurosporine in the serum-free medium for about 15 hours to induce cell apoptosis. In this method, the cells may comprise close to 100% confluent MSCs.

Above methods may be combined to induce cell apoptosis. For example, the starvation method may be combined with the UV irradiation method, and/or the thermal stress to induce apoptosis.

Example 2. Cell Apoptosis Detection

The cell apoptosis may be detected by using variety of methods. For example, the cell shrinkage and pyknosis may be detected by using a light microscope. Also, Annexin V and 7-AAD double positive apoptotic cells may be detected using flow cytometric analysis.

In one example, the cell apoptosis was induced by staurosporine. The cell apoptosis was detected by using the light microscope and the flow cytometric analysis. The results are shown in FIG. 1. Cell unattached from culture dish and shrinkage could be observed under light microscope. Compared with the control group, after staurosporine treatment, 7AAD+ or Annexin V+ or double positive apoptosis cell populations increased from 3.3% to 96.8%.

Example 3. Apoptotic Body Collection

Figure 2:
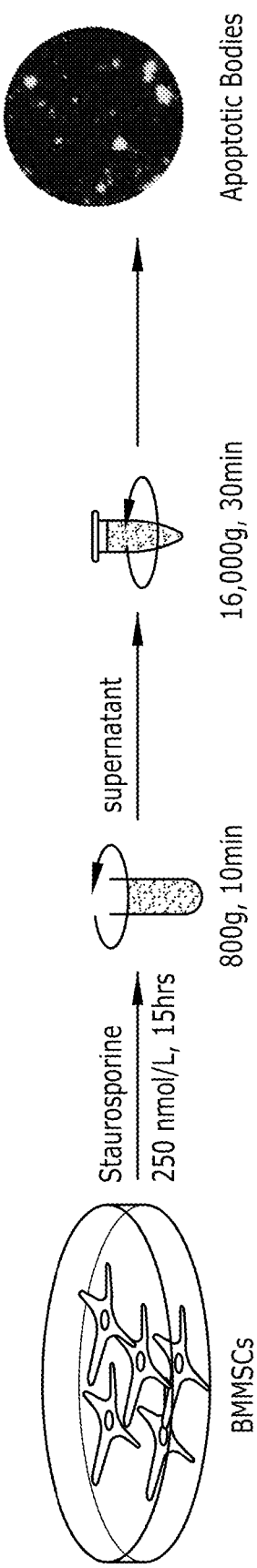
FIG. 2. Schematic demonstration of apoptotic body collection.

Culture medium from induced apoptotic cells was collected in a sterile centrifuge tube (about 15 ml in about 50 ml tube). First, the dead cells and the cell debris were removed by centrifugation at about 800 g for about 10 minutes. Then, the supernatant was transferred into about 1.5 ml EP tubes. The supernatant was further centrifuged at about 16,000 g for about 30 minutes to obtain the apoptotic bodies as a pellet. To eliminate the reagent or serum effect in the medium, the pellet was re-suspended and washed by PBS and re-centrifuged at about 16,000 g for about 30 minutes. This example is schematically shown in FIG. 2.

Example 4. Apoptotic Body Identification

Figure 3:
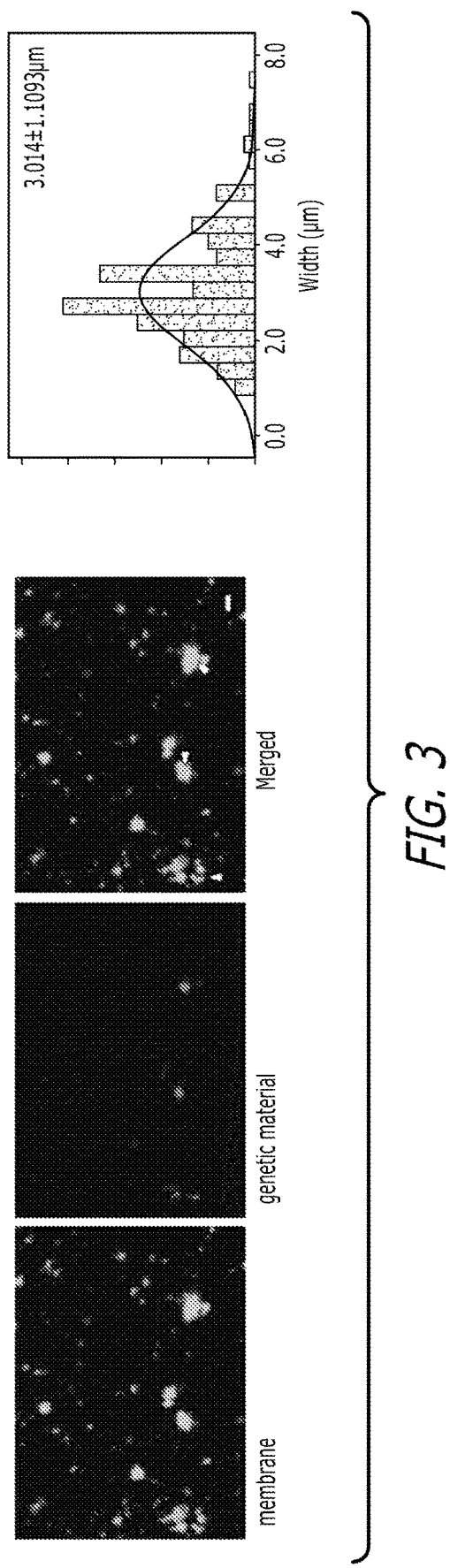
FIG. 3. Apoptotic body identification by fluorescent microscopy.

In this example, the apoptotic bodies were identified by using a fluorescent microscopy technique. The results are shown in FIG. 3. The membrane of apoptotic bodies were labeled with PKH26 and the genetic material was labeled with Hoechst 33342 as described in the manufacturer's instructions. The diameter of apoptotic bodies varied in the range of 0.5 µm to 10 µm, with the average size about 3.014±1.1093 µm. Less than 10% of apoptotic bodies contained genetic materials. Surface markers Annexin V, 7-AAD and TSP of apoptotic bodies may be identified by flow cytometric analysis.

Example 5. Apoptotic Body Quantitation and Purification

Figure 4:
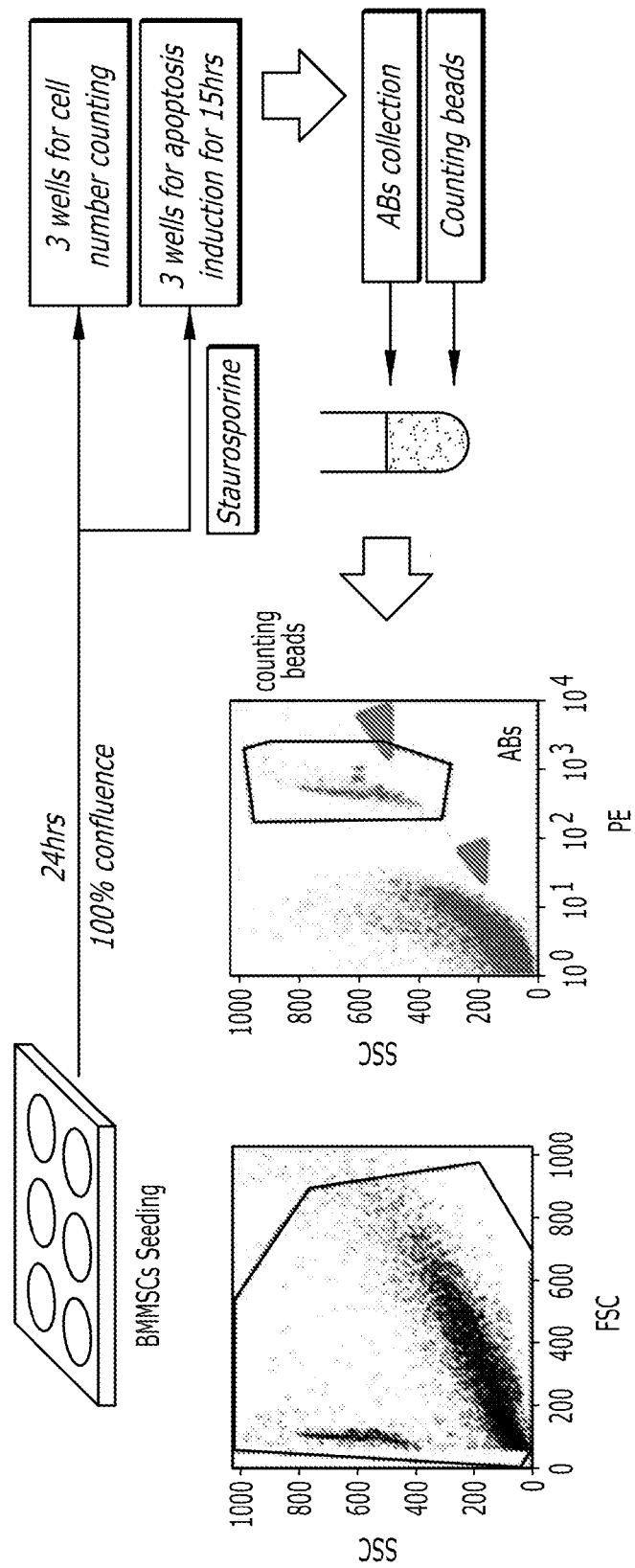
FIG. 4. Schematic demonstration of the relative counting method and an experimental result of an apoptotic body counting obtained by using this method.

A relative counting method was used for apoptotic body quantitation. First, a known amount of fluorescent dye labeled beads ("counting beads") were added into apoptotic body suspension. Then, the relative ratio of apoptotic bodies and counting beads were detected by using the flow cytometric analysis. This method is schematically demonstrated in FIG. 4. The number of apoptotic bodies were calculated based on the known amount of the counting beads according to the following formula:

$$AB = \frac{AB \text{ events in flow cytometry}}{\text{Counting bead events in flow cytometry}} \times \text{counting beads}$$

The harvest rate of apoptotic bodies to the cells varied in the range of 5 to 10.

Example 6. Apoptotic Body Purification by Flow Cytometric Purification

In this example, the apoptotic bodies were further purified by using the flow cytometric sorting technique. These purified apoptotic bodies may be used in preparation of the composition of this disclosure, wherein the apoptotic body may be the purified apoptotic body.

Figure 5A:
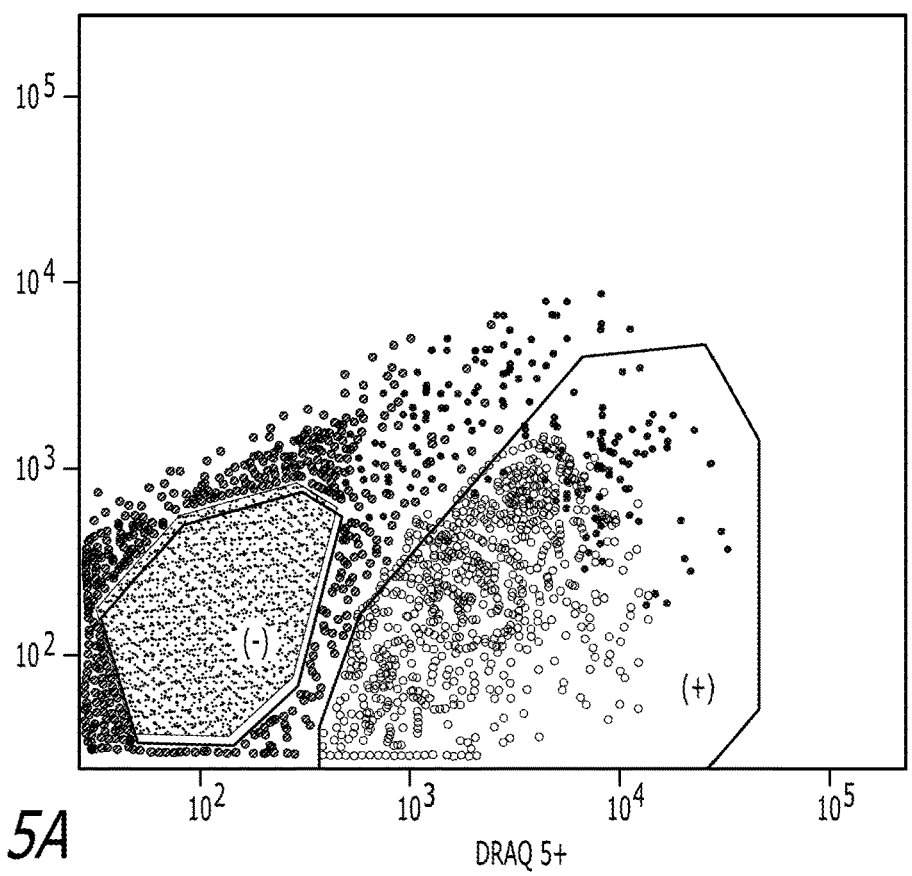
FIGS. 5A-B. Apoptotic body purification and sorting using the flow cytometric sorting method. DRAQ5 was used as fluorescent marker.
Figure 5B:
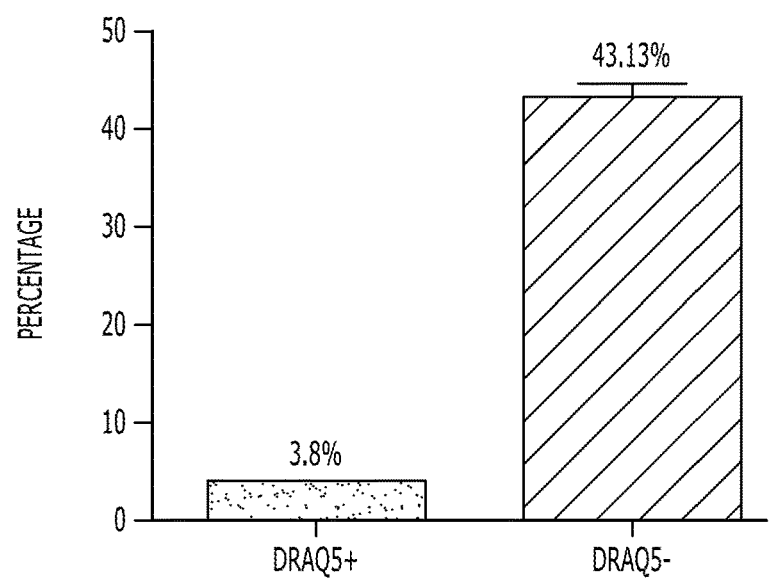

Genetic material in apoptotic bodies was labeled by DRAQ5 as the marker for the flow cytometric sorting. Apoptotic bodies were separated into two populations. Results are shown in FIGS. 5A-B. The DRAQ5 positive population contained apoptotic bodies with the genetic material and the DRAQ5 negative population contained apoptotic bodies with no genetic material. 3.8% apoptotic bodies with genetic material can be sorted out, meanwhile, 43.13% apoptotic bodies without genetic material can be collected during flow cytometric sorting.

Example 7. Apoptotic Body Purification by Differential Centrifugation

Figure 6:
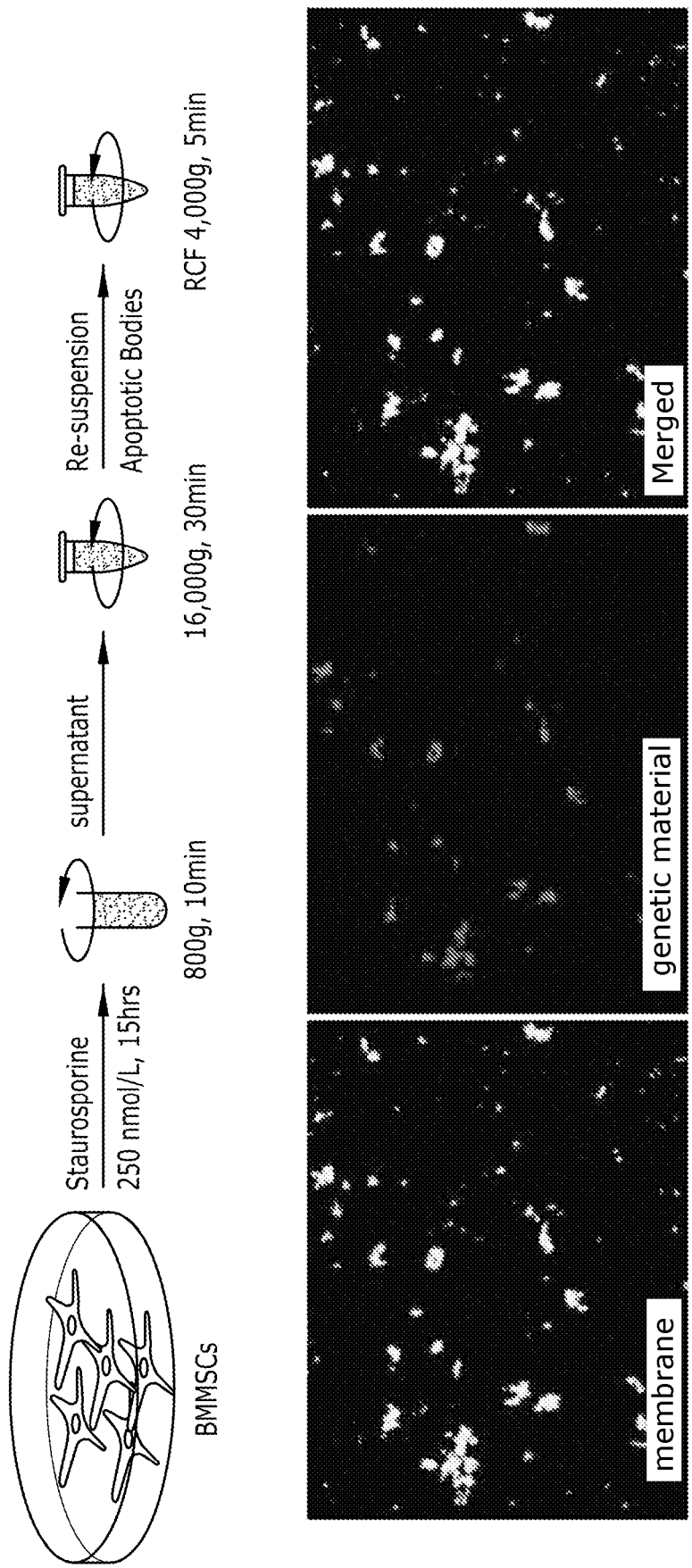
FIG. 6. Schematic demonstration of apoptotic body purification and microscopy of the cells purified by this method.

In this example, the apoptotic bodies were further purified by using the differential centrifugation technique. This method of purification of apoptotic bodies is schematically shown in FIG. 6. These purified apoptotic bodies may be used in preparation of the composition of this disclosure, wherein the apoptotic body may be the purified apoptotic body.

Based on the different sedimentation rate, large sized apoptotic bodies were separated using a low centrifugal force. First, the pelleted apoptotic bodies were re-suspended with PBS and then centrifuged at about 4,000 g for about 5 minutes. The diameters of pelleted apoptotic bodies varied in the range of 4 µm to 10 µm, and more than 80% of apoptotic bodies contained genetic material. The results are shown in FIG. 6.

Example 8. Apoptotic Bodies Improve BMMSC Colony Forming Numbers In Vivo

Figure 7B:
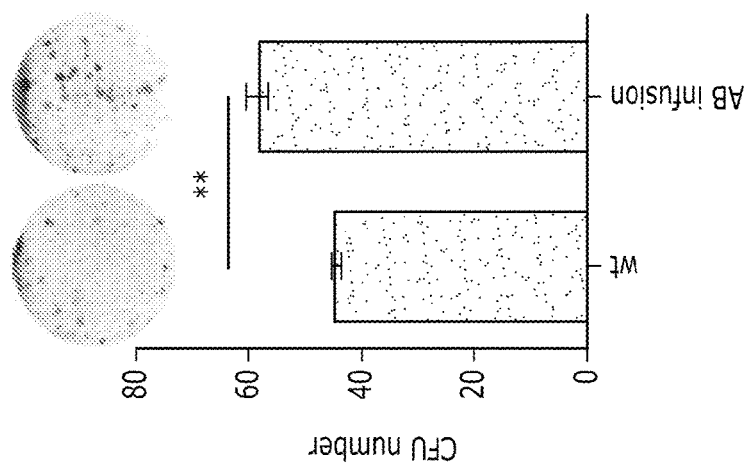
FIGS. 7A-B. Schematic demonstration of systemic infusion of a mouse by apoptotic bodies and harvesting of BMMSCs. Experimental CFU numbers are shown in this figure.
Figure 7A:
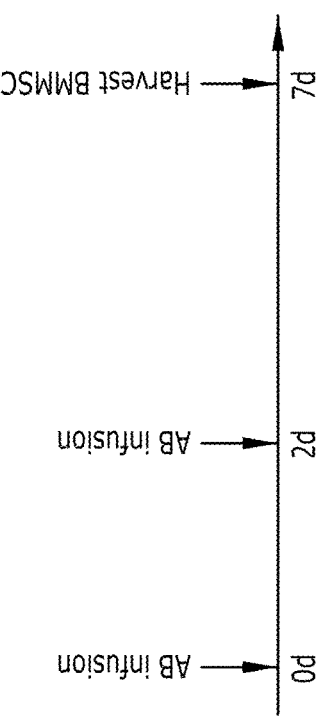
Figure 7A:
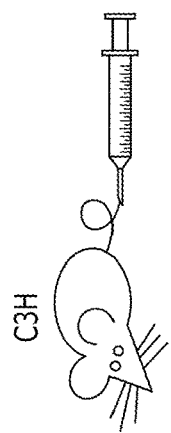

C3H mice were subjected to systemic infusion with apoptotic bodies at day 0 and day 2. The dose of each systemic infusion was 5×10$^6$ apoptotic body cells. BMMSCs were harvested from the mice at day 7. The mice infused with apoptotic bodies generated higher numbers of BMMSC CFU-F than wild type (wt) mice did, as shown by toluidine blue staining. The CFU-F numbers of apoptotic bodies treatment group increased from 42 colonies/1 million cells to 57 colonies/1 million cells. See FIGS. 7A-B. These experimental results demonstrated that apoptotic bodies can improve BMMSC colony forming numbers in vivo.

Example 9. Apoptotic Bodies Improve BMMSC Colony Forming Numbers in Vitro

Figure 8A:
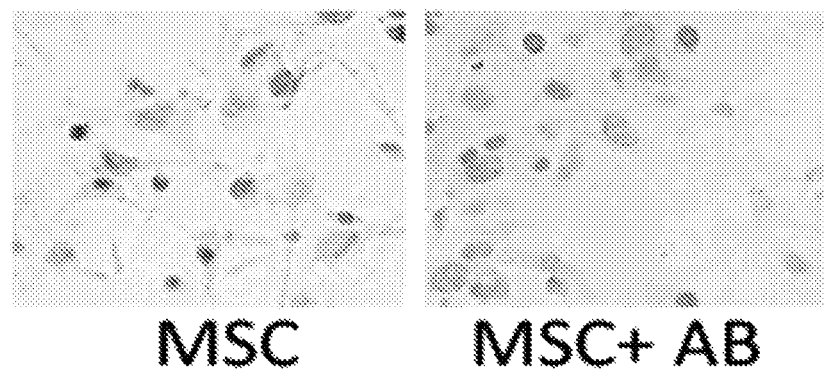
FIGS. 8A-B. BMMSC proliferation in vitro by apoptotic body treatment. (A) Cell microscopy and (B) cell percentage.
Figure 8B:
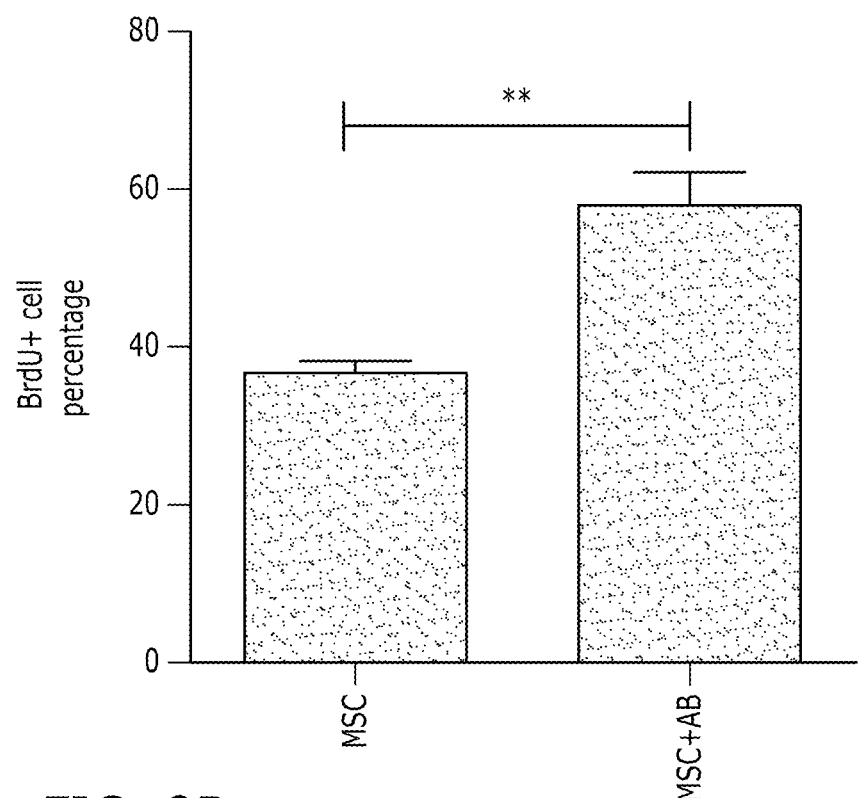

In this example, BMMSCs were treated with apoptotic bodies and analyzed by incorporation of a BrdU assay. It was found that the number of BrdU-positive (BrdU$^+$) cells significantly increased in BMMSCs treated with the apoptotic bodies when compared with that of untreated BMMSCs. See FIGS. 8A-B. These experimental results demonstrated that apoptotic bodies can improve BMMSC colony forming numbers in vitro.

Example 10. Apoptotic Bodies Improve Osteogenesis of BMMSCs In Vitro

Figure 9B:
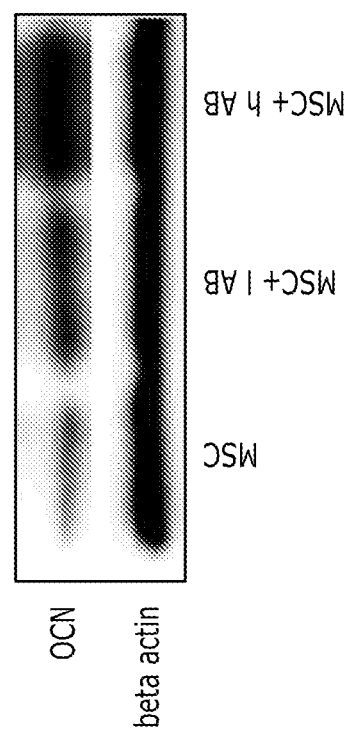
FIGS. 9A-B. Osteogenic differentiation potential of the BMMSCs treated with apoptotic bodies in vitro. (A) Alizarin staining and (B) Immunoblot analysis.
Figure 9A:
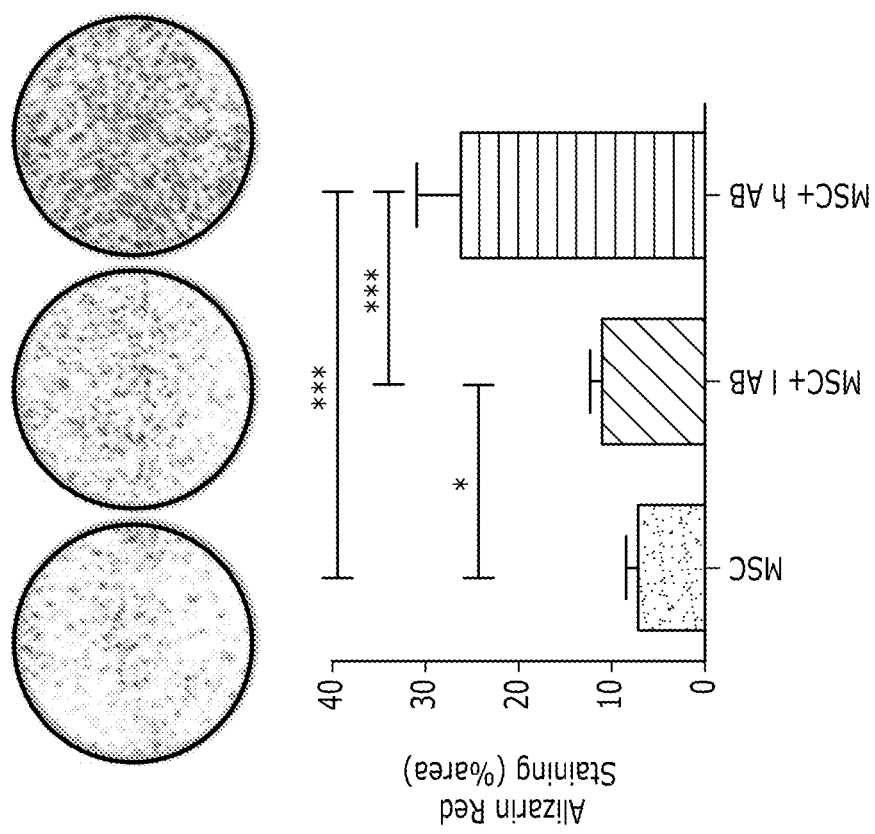

In this example, the BMMSCs were treated with apoptotic bodies in vitro. The osteogenic differentiation potential of BMMSCs were assessed at six weeks after the osteogenic induction by Alizarin red staining. The Alizarin-red-positive (Alizarin Red+) area, in terms of mineralization nodes, was calculated as a percentage of total area. Immunoblot analysis revealed that expression levels of OCN had the same trend. The experimental results are shown in FIGS. 9A-B.

The BMMSCs treated with the high-dose of apoptotic bodies formed significantly increased amounts of mineralized nodules as compared with those of the untreated BMMSCs and the BMMSCs treated with the low-dose of apoptotic bodies. These experimental results demonstrated that the osteogenic differentiation potential of BMMSCs can be improved by apoptotic body treatment in vitro. These experimental results further demonstrated that this improvement potential can be increased by increasing the dose of the apoptotic bodies.

Example 11. Apoptotic Bodies Improve Osteogenesis of BMMSCs In Vivo

Figure 10B:
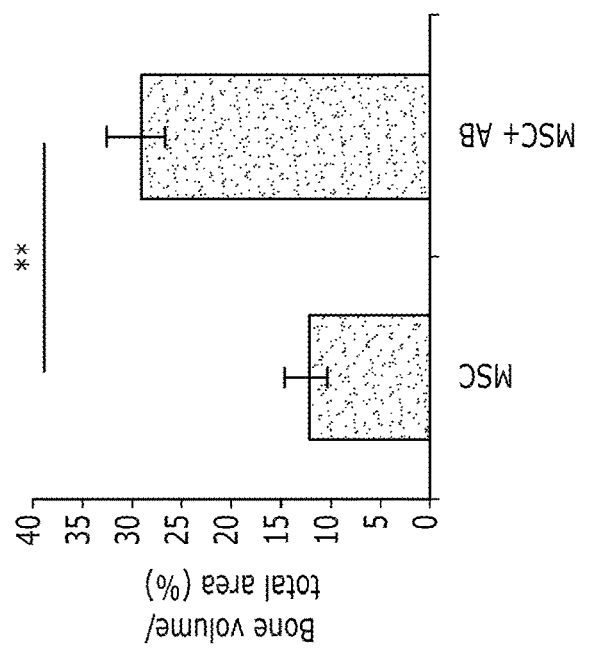
FIGS. 10A-B. Mineralized tissue formation potential of the BMMSCs treated with the apoptotic bodies. (A) Tissue microscopy and (B) Bone volume area.
Figure 10A:
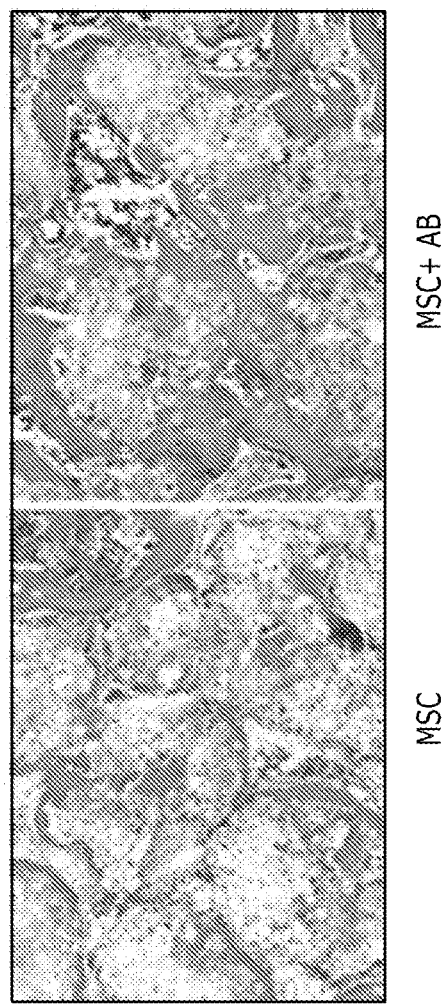

In this example, the BMMSCs treated with the apoptotic bodies in vitro were transplanted subcutaneously into immunocompromised mice by using hydroxyapatite tricalcium phosphate (HA/TCP) as a carrier. Experimental results shown in FIGS. 10A-B indicated that the BMMSCs treated with the apoptotic bodies formed more mineralized tissue when compared with the untreated BMMSCs. These experimental results demonstrated that the mineralized tissue formation potential of BMMSCs can be improved by their in vivo treatment with the apoptotic bodies.

Example 12. Apoptotic Bodies Improve Adipogenesis of BMMSCs In Vitro

Figure 11B:
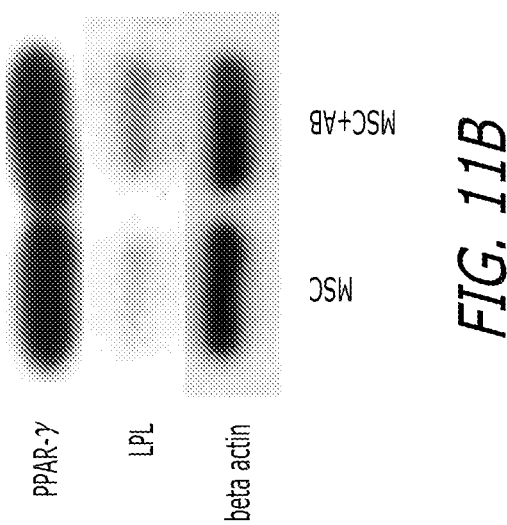
FIGS. 11A-B. Adipogenesis potential of the BMMSCs treated with the apoptotic bodies. (A) Oil-red O staining and (B) Immunoblot analysis.
Figure 11A:
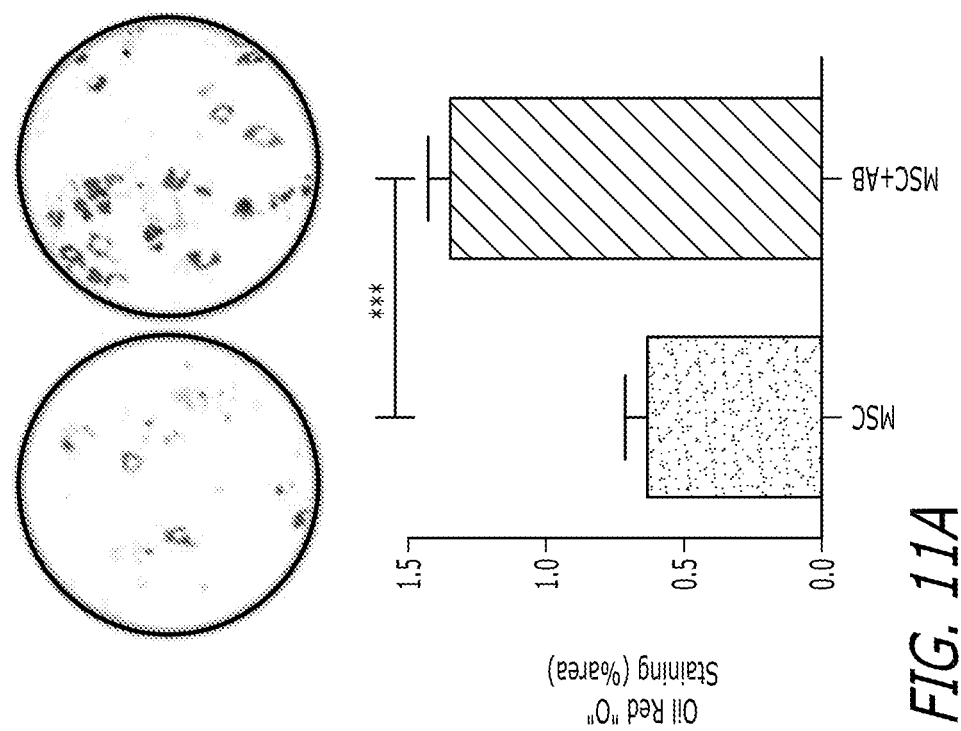

In this example, the BMMSCs were treated with apoptotic bodies in vitro. The adipogenesis potential of the BMMSCs were assessed at four weeks after the adipogenesis induction by Oil-red 0 staining. Numbers of Oil-red 0-positive (Oil-Red-O+) cells were calculated as a percentage of total cells. The experimental results shown in FIGS. 11A-B indicated that the BMMSCs treated with the apoptotic bodies had an elevated potential to differentiate into adipocytes. Immunoblot assay indicated that the expression levels of adipocyte-specific molecules LPL and PPARγ2 had the same trend. These experimental results demonstrated that the adipogenesis potential of the BMMSCs can be improved by their in vitro treatment with the apoptotic bodies.

Example 13. Apoptotic Bodies Improve Immunomodulation of BMMSCs In Vitro

BMMSC can directly induce active T cells apoptosis as the immunomodulation properties. BMMSC/T-cell co-culture system showed that apoptotic bodies treated BMMSCs had significantly increased capacity to induce AnnexinV+ 7AAD+ double positive apoptotic T cells, when compared to the untreated BMMSCs. Experimental results are shown in FIGS. 12A-B.

Example 14. Apoptotic Bodies have Therapeutic Effect on Inductive Colitis Mice

In this example, first group of mice with DSS-induced experimental colitis were infused with a dose of $5 \times 10^6$ apoptotic bodies ("AB infusion"). For the positive control, a second group of mice with DSS-induced experimental colitis were infused with a dose of $5 \times 10^5$ BMMSCs ("MSC infusion"). A third group of mice with DSS-induced experimental colitis were left untreated ("colitis"). The first and the second mice groups were infused three days after the induction of the colitis. Weights loss of three mice groups were recorded over a period of 10 days, starting from the induction of the colitis. Results are shown in FIGS. 13A-D.

The apoptotic body treatment exerted more significant restoration of disease phenotype, body weight loss, in the colon and reduction of histological activity index compared with those of the colitis group. Compared with the colitis group, the apoptotic body treatment showed a significant effect in reducing the levels of Th17 cells in the mice at 10 days post-colitis induction. These experimental results demonstrated that the apoptotic bodies can be used in the treatment of immune disorder diseases like colitis.

Example 15. Apoptotic Bodies have Therapeutic Effect on Ovariectomized Mice

In this example, a first group of ovariectomized mice were infused with a dose of $5 \times 10^6$ apoptotic bodies ("OVX+ AB"). For the positive control, a second group of ovariectomized mice were infused with a dose of $5 \times 10^5$ BMMSCs ("OVX+MSC"). A third group of ovariectomized mice were left untreated ("OVX"). A fourth group of non-ovariectomized mice were also left untreated ("Sham"). The first and the second mice groups were infused two weeks after the induction of the ovariectomy. Results are shown in FIGS. 14A-I.

Hematoxylin and eosin (HE) staining showed that both the BMMSC and the apoptotic body treatment significantly rescued the bone loss in ovariectomized mice. The apoptotic body treatment significantly improved bone mineral density (BMD) in femurs BV/TV compared to that of the untreated ovariectomized mice. Also, the apoptotic body infusion rescued CFU-F numbers, population doublings, osteogenesis capability and adipogenesis capability of OVX-derived bone marrow MSCs. Meanwhile, the apoptotic body infusion reduced the level of Th1 and Th17 t cells.

Example 16. Apoptotic Bodies have Therapeutic Effect on Systemic Lupus Erythematosus (SLE) Mice In this example, MRL/lpr mice was used as a systemic lupus erythematosus model. A first group of MRL/lpr mice were infused with apoptotic bodies ("Lpr+AB"). For the positive control, a second group of MRL/lpr mice were infused with BMMSCs ("Lpr+MSC"). A third group of MRL/lpr mice were left untreated ("lpr"). A fourth group of C3H mice were also left untreated ("C3H"). Results are shown in FIGS. 15A-G.

The apoptotic body infusion rescued mesenchymal stem cell (MSC) functional deficiency and reconstructed trabecular bone structure of MRL/lpr mice. The apoptotic body infusion significantly improved bone mineral density (BMD) in femurs BV/TV compared to that of the untreated MRL/lpr mice. The apoptotic body infusion reduced levels of autoantibodies and improved renal function in MRL/lpr mice. Levels of C3, anti-dsDNA in peripheral blood decreased in the apoptotic body infused group compared with those of the untreated group, while albumin level was rescued. The apoptotic body infusion reduced Th17 T cell level and recovered Treg/Th17 ratio.

Example 17. Apoptotic Bodies have Therapeutic Effect on Tumor

The therapeutic effect of apoptotic bodies was evaluated in both solid tumors and hematopoietic tumor. For this evaluation, the mouse tumor models of hepatocellular carcinoma and multiple myeloma were established.

For mouse model of hepatocellular carcinoma, xenografts of hepatocellular carcinoma were generated by intramuscular injection of HepG2 cells. Briefly, the mouse model was conducted in weight-matched, about 8-week-old female NOD/SCID mice (Jackson Lab, Bar Harbor, Me., USA). HepG2 hepatocellular carcinoma cells (ATCC, Manassas, Va., USA) were cultured in Dulbecco's Modified Eagle Medium (Invitrogen Co., Carlsbad, Calif., USA) supplemented by about 10% fetal bovine serum (Summit Biotechnology, Fort Collins, Colo., USA) and antibiotics (Invitrogen Co., Carlsbad, Calif., USA) at about 37° C., about 5% $CO_2$ HepG2 cells (about $1 \times 10^6$ cells/10 grams body weight) suspended in PBS were injected intramuscularly in the hind legs of NOD/SCID mice and PBS injection served as negative control.

To test the effect of apoptotic bodies on in situ carcinoma, diethylnitrosamine as a carcinogen was injected in B6C3F1 mice for induction of in situ hepatocelluar carcinoma.

Briefly, about 4 week old B6C3F1 male mice were used to generate the carcinoma model. A single dosage of diethylnitrosamine (about 100 mg/gram body weight) was intraperitoneally administrated to the mice.

For multiple myeloma model, the 5TGM1 MM cell line, subcloned from a stroma-independent cell line from parent murine 5 T33 (IgG2bκ) multiple myeloma, was grown in long-term suspension culture in Isocove's modified Dulbecco's medium (Invitrogen Co., Carlsbad, Calif., USA) with about 10% fetal bovine serum and antibiotics. 5TGM1 multiple myeloma model was conducted in weight-matched about 10-week-old female NOD/SCID mice. The mice were housed in isolator cages, and autoclaved chow and acidified water were provided ad libitum. Disseminated multiple myeloma was induced by the intravenous inoculation of 5TGM1 cells (about $6\times10^6$/10 grams body weight) in about 200 µl PBS through the tail vein.

The apoptotic bodies were delivered in vivo as follows. Mouse with xenograft tumors of hepatocellular carcinoma and multiple myeloma were randomized to treated group and control group. After tumor cell inoculation for about 1 week, a single dose of apoptotic bodies (about $3\times10^6$/10 grams body weight) were delivered via tail vein injection (treated group) and PBS injection served as control.

For mouse models of in situ hepatocellular carcinoma, apoptotic bodies (about $3\times10^6$/10 grams body weight) were monthly administrated into the mice via tail vein.

The therapeutic effects of the apoptotic bodies were assessed as follows. Xenograft tumors of hepatocellular carcinoma were surgically harvested about 4 weeks after tumor inoculation. The therapeutic effect of apoptotic bodies was assessed by measuring the volume of the tumors by the formula: volume=length×width$^2$×0.52. To reveal the histology of the tumors with or without apoptotic body treatment, the tissue was fixed in about 4% paraformaldehyde for about 48 hours and subsequently embedded in paraffin for Hematoxyin-Eosin staining.

For assessment of the therapeutic effects of apoptotic bodies in multiple myeloma models, the 8-week survival rates of the mice in different groups were compared. The results were analyzed by Kaplan-Meier survival method.

In vivo cytotoxicity of the apoptotic bodies on tumor cells were determined as follows. HepG2 hepatocellular carcinoma cells were seeded in 24-well plate at the concentration of about $1\times10^5$ cells/well. About 12 hours after cell seeding, the cells were treated by apoptotic bodies (about $1\times10^6$ apoptotic bodies/well) or PBS and different concentration of apoptotic bodies was applied in the cell culture for evaluation of the cytotoxicity. The cell survival was assayed by an automated cell counter (Bio-rad, Hercules, Calif., USA) about 2 days after the treatment of apoptotic bodies and dead cells were excluded by staining of trypan blue (Invitrogen Co., Carlsbad, Calif., USA).

Figure 16A:
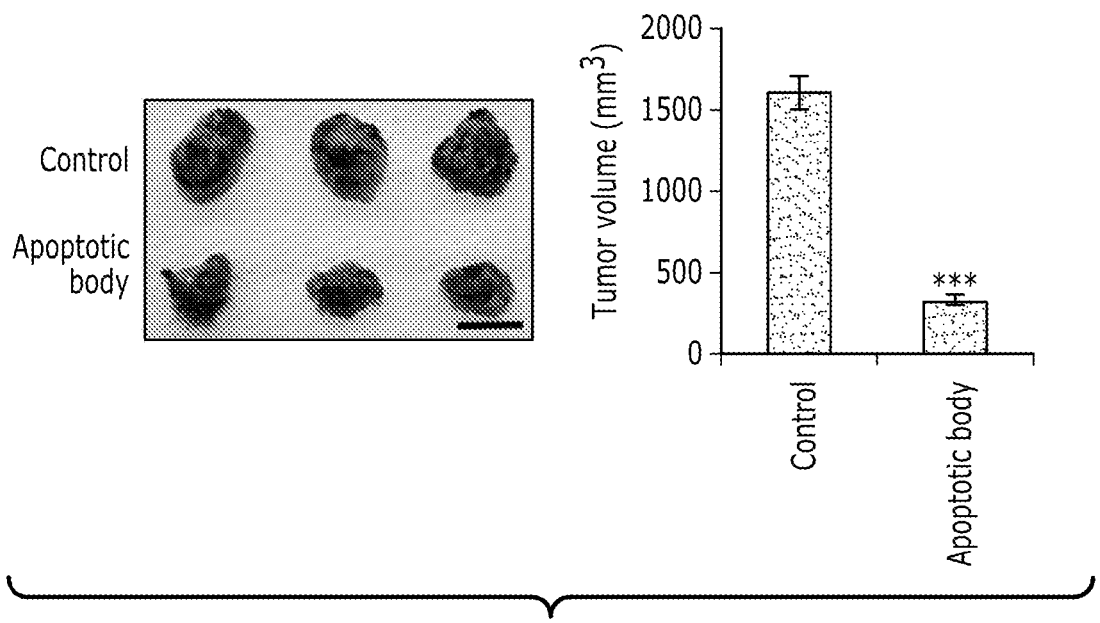
FIGS. 16A-B. Apoptotic body infusion inhibited solid tumor growth in mouse model of hepatocellular carcinoma. (A) Xenograft tumors with apoptotic body treatment showed reduced tumor volume. (B) HE staining showed apoptotic body-treated tumor induced infiltration of hematopoietic cells compared to control tumor.
Figure 16B:
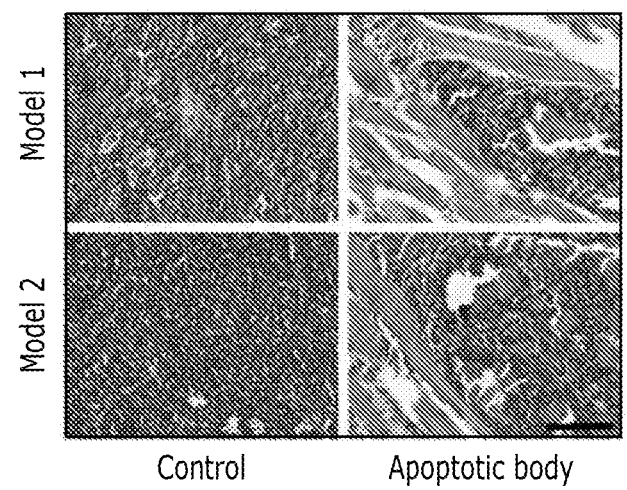
Figure 17A:
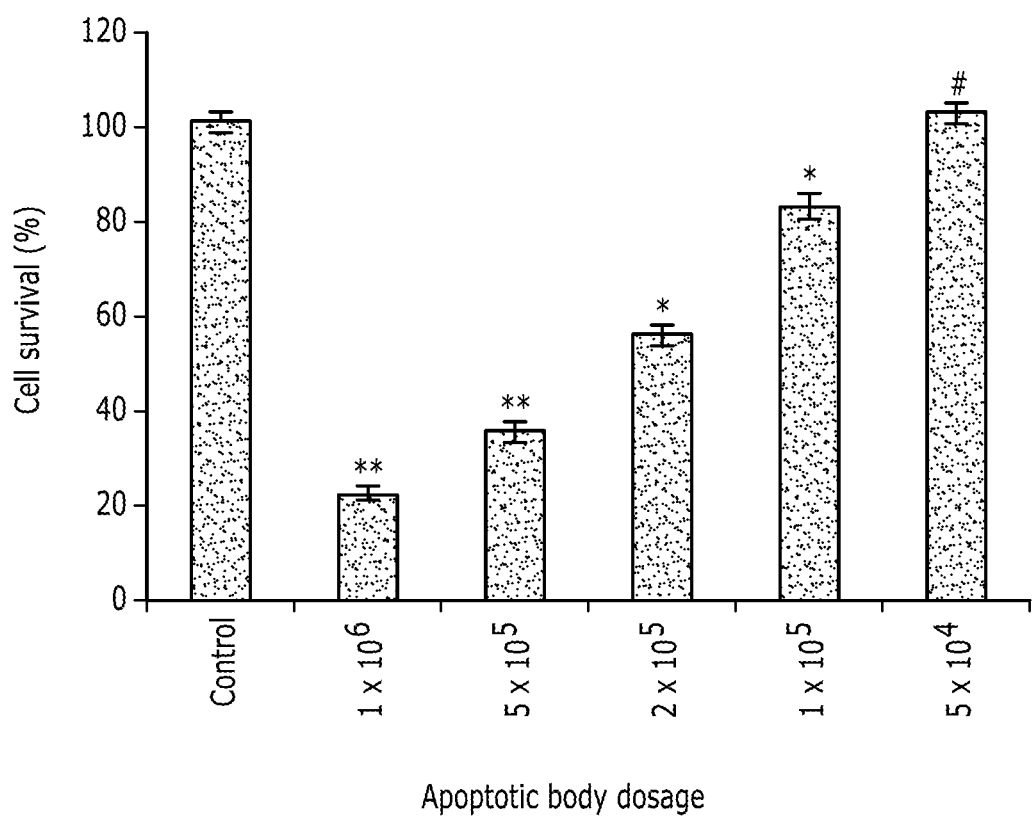
FIGS. 17A-B. Apoptotic body treatment reduced in vitro tumor cell survival. (A) Cell survival analysis indicated co-culture with apoptotic bodies reduced the tumor cell survival in a dosage-dependent manner. (B) Microarray analysis of global gene expression pattern indicated apoptotic body treatment increased the cell apoptosis and lysosome function.
Figure 17B:
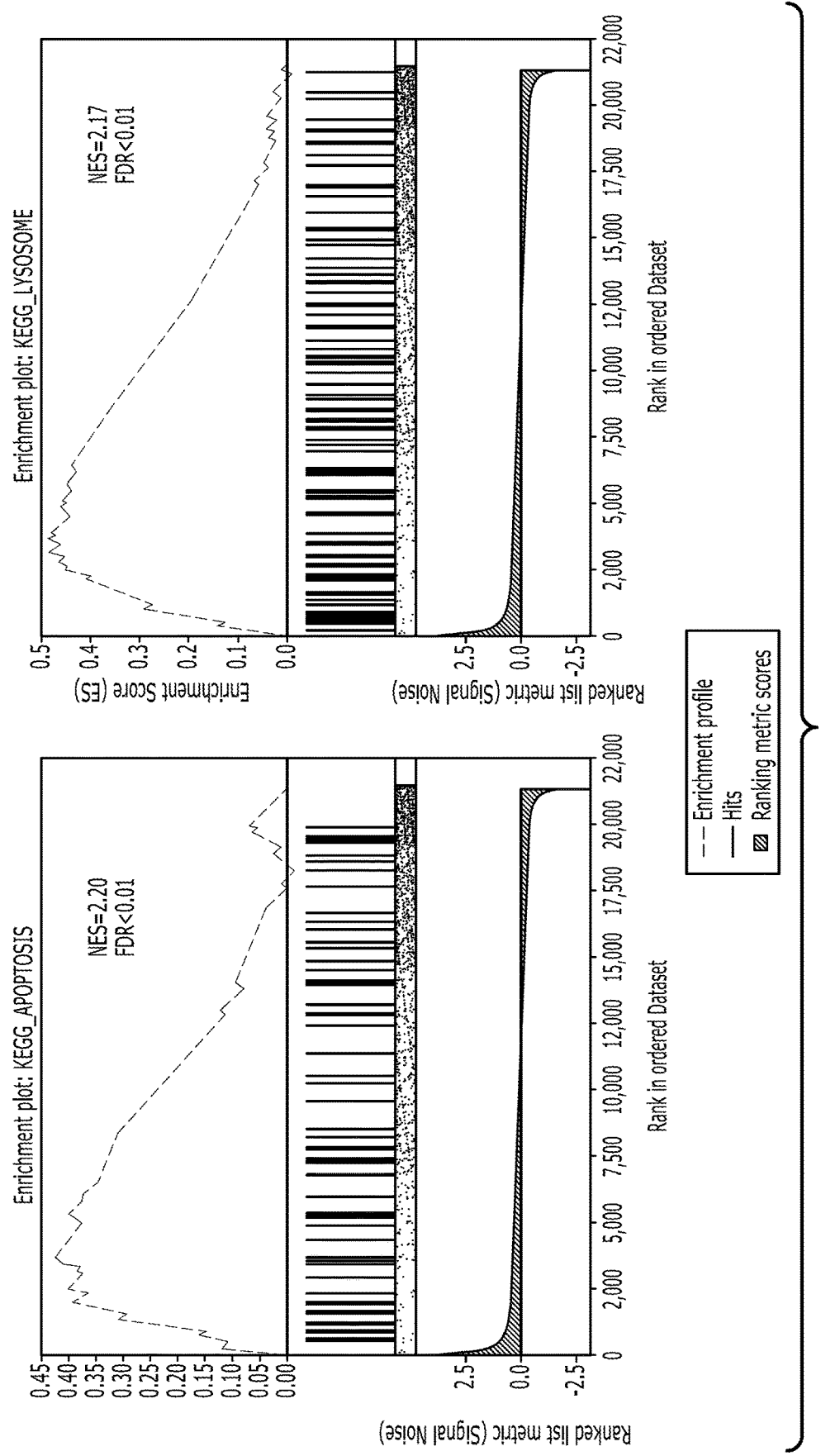

Results of the apoptotic treatment of tumors were as follows. Intramuscular inoculation of HepG2 cells successfully generated tumor growth in NOD/SCID mice. To test the therapeutic effect in the tumor model, apoptotic bodies were systemically infused into the mice with xenograft tumor. The results of tumor volume measurement showed that tumors in the mice that received apoptotic body treatment were significantly smaller than that in the mice without the treatment (FIG. 16A). Xenograft tumors generated by HepG2 cells were filled by progressive tumor cell growth and after apoptotic body treatment, the tumors were infiltrated by hematopoietic cells with large area of necrosis (FIG. 16B). To confirm the therapeutic effect, in vitro co-culture assay indicated obvious cytotoxicity of apoptotic bodies to HepG2 cells, which was in a dosage-dependent manner (FIG. 17A). Comparison of global gene expression pattern indicated after apoptotic body treatment, the tumor cells underwent enhanced function of apoptosis and lysosome (FIG. 17B).

Figure 18:
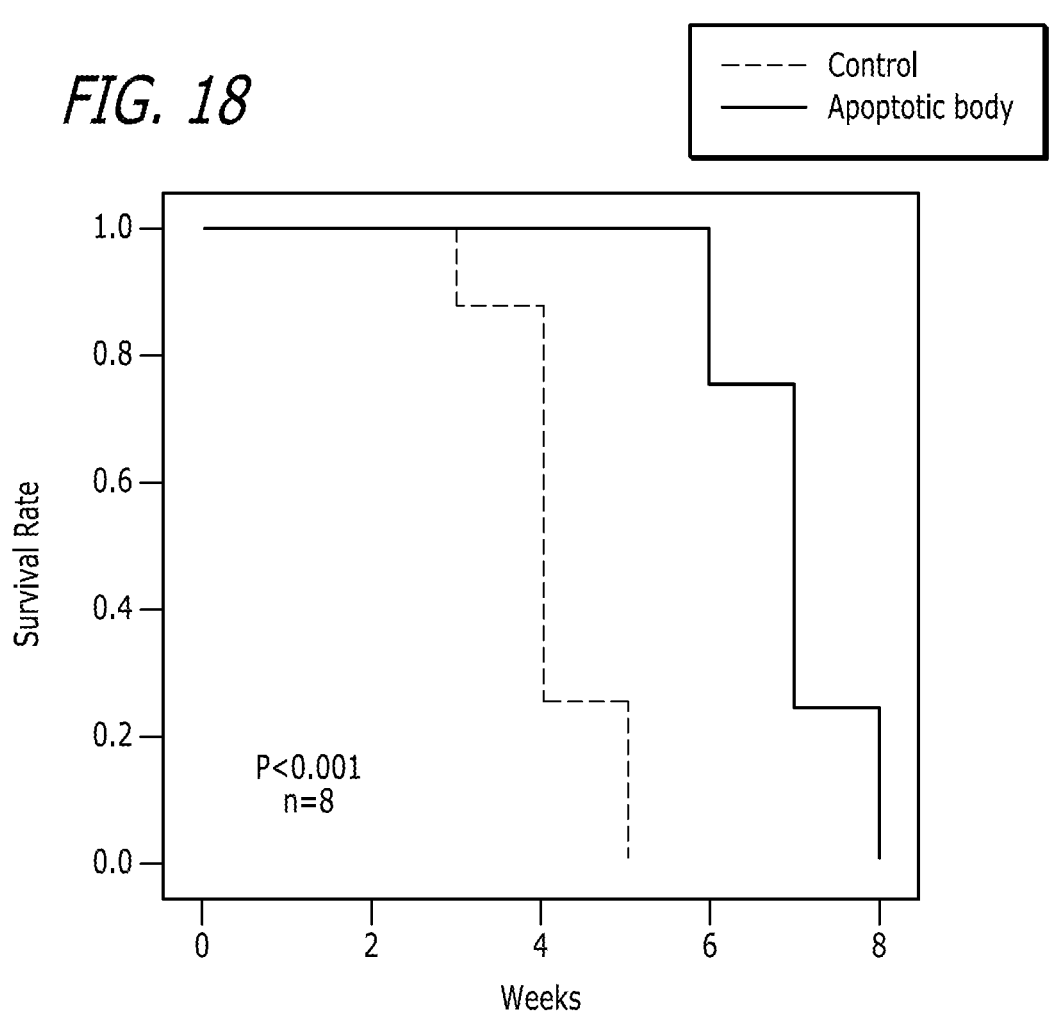
FIG. 18. Apoptotic body infusion improved the survived rate of mouse models of multiple myeloma. Kaplan-Meier survival analysis of the mouse models indicated apoptotic body treatment significant improved the mouse life span.
Figure 19A:
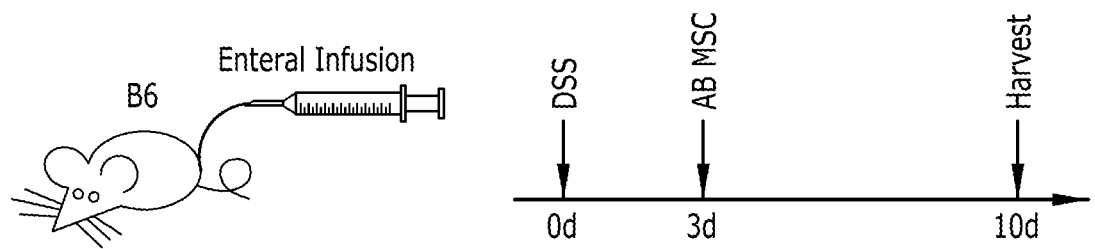
FIGS. 19A-E. Apoptotic body (AB) enteral infusion improves DSS-induced colitis. (A) Since DSS administration can induce colitis in mice, we infused about $1 \times 10^7$ AB or bone marrow mesenchymal stem cells (MSCs) at about 3 days post DSS induction and harvest samples at about 10 days post DDS induction to evaluate therapeutic effect of AB and use MSC enteral infusion as a positive control. The apoptotic body treatment showed: (B) significant therapeutic effect than MSC group in rescuing body weight and (C) reduction of histological activity index in the colon and reduction. (D and E) Compared with the colitis group, AB treatment showed a significant effect in reducing the levels of Th1 and Th17 cells in the mice at about 10 days post-colitis induction. These experimental results demonstrate that AB enteral infusion can be used as a novel approach in the treatment of immune disorder such as colitis.
Figure 19B:
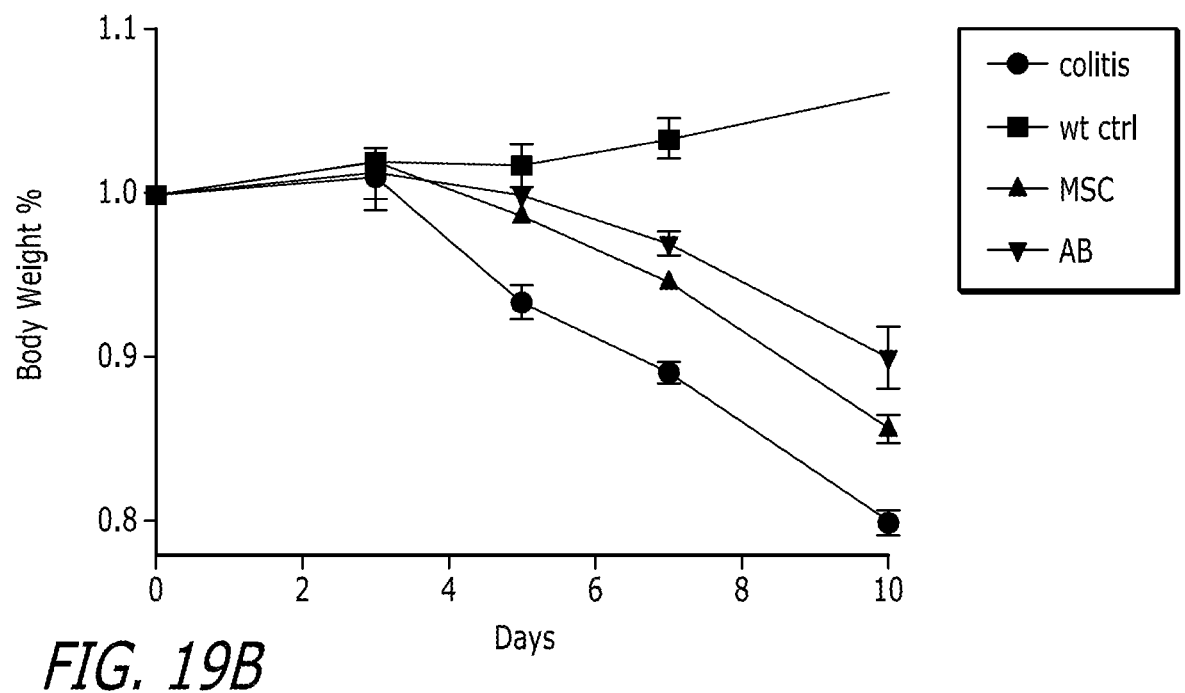
Figure 19C:
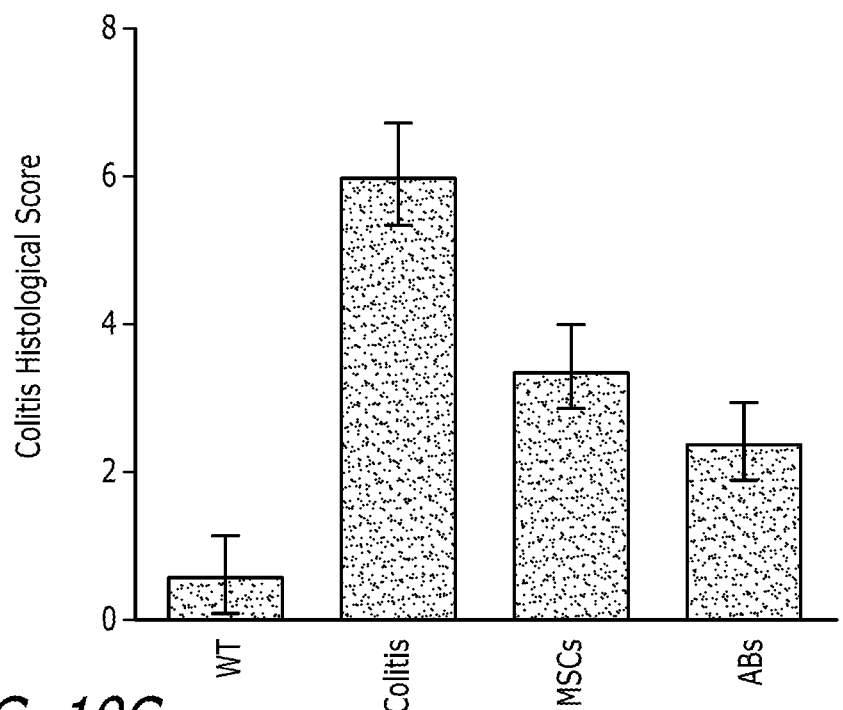
Figure 19D:
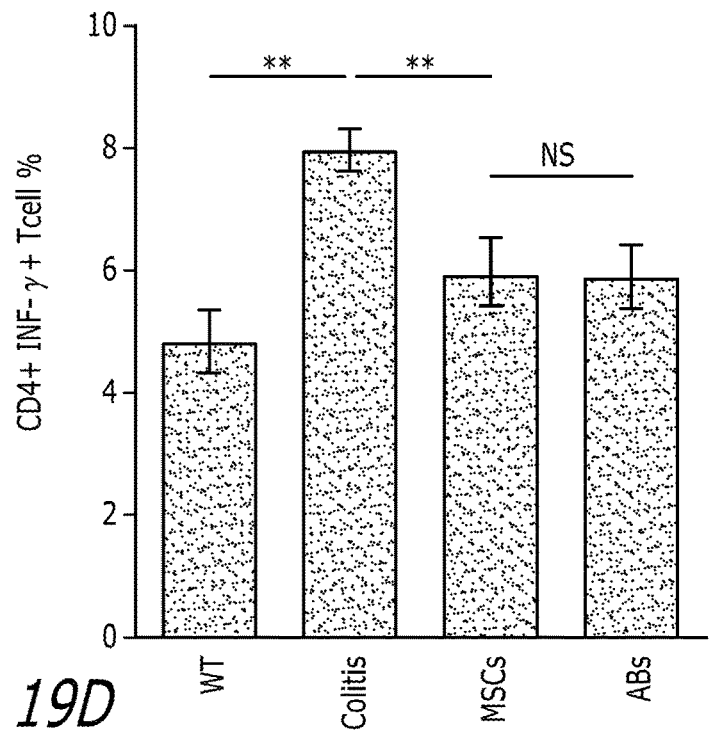
Figure 19E:
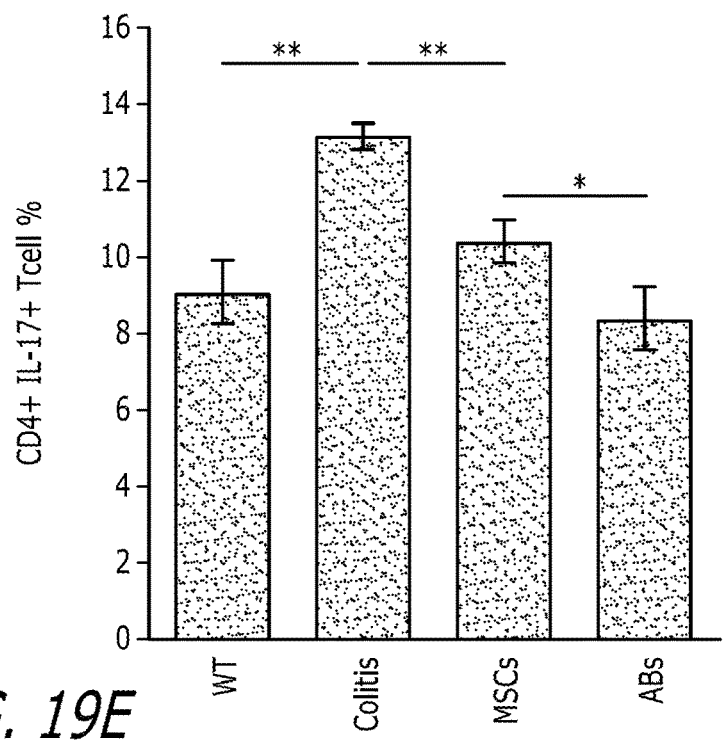

In mouse model of multiple myeloma, the mice that received systemic apoptotic body infusion survived significantly longer than control mice, indicating the therapy effectively inhibit the disease progression (FIG. 18).

Example 18. Apoptotic Body Enteral Infusion Improves Colitis

Apoptotic body (AB) infusion improves DSS-induced colitis, as shown in FIG. 19. Since DSS infusion can induce colitis in mice, we infused about $1\times10^7$ AB or bone marrow mesenchymal stem cells (MSCs) enterally at about 3 days post DSS induction and harvest samples at about 10 days post DDS induction to evaluate therapeutic effect of AB and use MSC infusion as a positive control (FIG. 19A). The apoptotic body treatment showed significant therapeutic effect than MSC group in rescuing body weight (FIG. 19B). The apoptotic body treatment also showed reduction of histological activity index in the colon (FIG. 19C). Compared with the colitis group, AB treatment showed a significant effect in reducing the levels of Th1 and Th17 cells in the mice at about 10 days post-colitis induction (FIGS. 19D-E). These experimental results demonstrated that AB infusion can be used as a novel approach in the treatment of immune disorder such as colitis.

Example 19. Apoptotic Body Infusion Improves Wound Healing

Figure 20A:
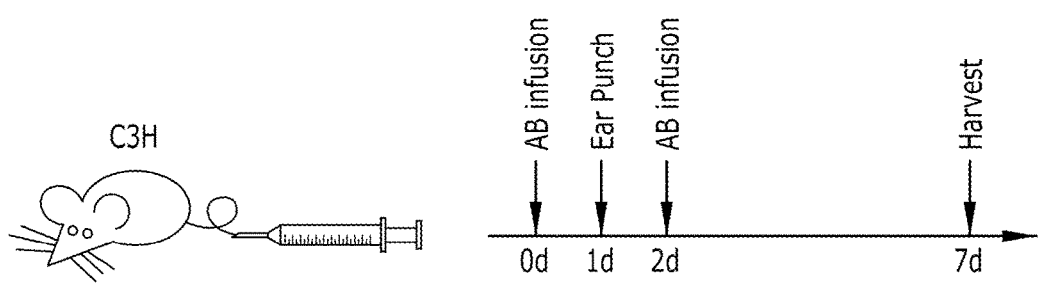
FIGS. 20A-C. AB infusion improves wound healing in mouse ear punch model. (A) about $5 \times 10^6$ AB was infused into mice wither before or after the ear punch. (B and C) Ear hole area of AB-treated group was significantly reduced when compared to un-treated control group at about 7 days post ear punch.
Figure 20B:
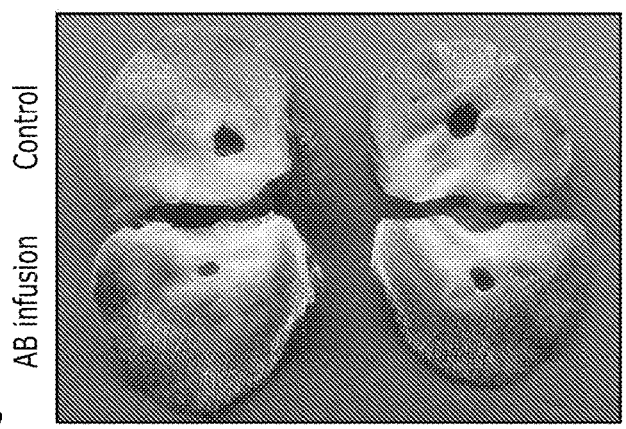
Figure 20C:
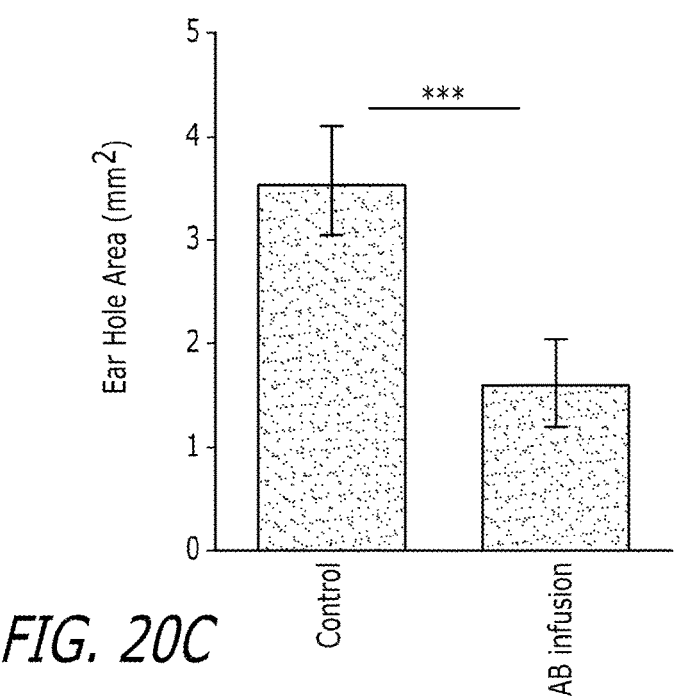

AB infusion improves wound healing in mouse ear punch model, as shown in FIGS. 20A-C. About $5\times10^6$ AB was infused into mice wither before or after the ear punch (FIG. 20A). Ear hole area of AB-treated group was significantly reduced when compared to un-treated control group at about 7 days post ear punch (FIG. 20B-C).

Any combination of products such as compositions comprising apoptotic bodies, methods of their preparation, and methods of their use that are described herein may also be made and followed.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

In this disclosure, the indefinite article "a" and phrases "one or more" and "at least one" are synonymous and mean "at least one".

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A composition comprising about $1\times10^1$ apoptotic bodies to about $1\times10^{10}$ apoptotic bodies and a carrier, wherein the apoptotic bodies comprise apoptotic mesenchymal stem cells, and wherein the apoptotic mesenchymal stem cells are:
   (i) positive for expression of thrombospondin-1 (TSP-1) and positive for staining by 7-amino-actinomycin D (7-AAD);
   (ii) positive for nucleic acid staining by a dye selected from the group consisting of 1,5-bis{[2-(di-methylamino)ethyl]amino}-4,8-dihydroxyanthracene-9,10-dione (DRAQ5) and 7-AAD;
   (iii) positive for staining by DRAQ5, Annexin V and 7-AAD;
   (iv) positive for staining by 7-AAD and Annexin V; and
   (v) positive for expression of TSP-1 and positive for staining by Annexin V and 7-AAD.

2. The composition of claim 1, wherein the apoptotic mesenchymal stem cell comprises an apoptotic bone marrow-derived mesenchymal stem cell, an apoptotic dental pulp mesenchymal stem cell, an apoptotic mesenchymal stem cell from human exfoliated deciduous teeth, an apoptotic periodontal ligament mesenchymal stem cell, an apoptotic dental follicle mesenchymal stem cell, an apoptotic tooth germ progenitor mesenchymal stem cell, an apoptotic mesenchymal stem cell from the apical papilla, an apoptotic oral epithelial progenitor/mesenchymal stem cell, an apoptotic gingiva-derived mesenchymal stem cell, an apoptotic periosteum-derived mesenchymal stem cell, an apoptotic salivary gland-derived mesenchymal stem cell, or a combination thereof.

3. The composition of claim 1, wherein the apoptotic mesenchymal stem cell comprises an apoptotic body derived from cultured mesenchymal stem cell, an apoptotic body derived from an uncultured gingiva-derived mesenchymal stem cell, an apoptotic dental pulp mesenchymal stem cell, an apoptotic bone-marrow-derived mesenchymal stem cell, or a combination thereof.

4. The composition of claim 1, wherein the apoptotic mesenchymal stem cell is obtained by the apoptosis of a stem cell induced by a starvation method, an ultra-violet irradiation method, a thermal stress method, a staurosporine method, or a combination thereof.

5. The composition of claim 1, wherein the apoptotic mesenchymal stem cell is obtained by incubating a stem cell in a serum-free medium for a time period in the range of 1 hour to 1,000 hours.

6. The composition of claim 1, wherein the apoptotic mesenchymal stem cell is obtained by incubating a stem cell is in a serum-free medium for a time period in the range of 10 hours to 100 hours.

7. The composition of claim 1, wherein the apoptotic mesenchymal stem cell is obtained by heating a stem cell at a temperature in the range of 30° C. to 100° C. for a predetermined period of time.

8. The composition of claim 1, wherein the apoptotic mesenchymal stem cell is obtained by heating a stem cell at a temperature in the range of 30° C. to 100° C. for a time period in the range of 1 minute to 1,000 minutes.

9. The composition of claim 1, wherein the apoptotic mesenchymal stem cell is obtained by heating a stem cell at a temperature in the range of 30° C. to 100° C. for a time period in the range of 10 minutes to 100 minutes.

10. The composition of claim 1, wherein the apoptotic mesenchymal stem cell is obtained by heating a stem cell at a temperature in the range of 40° C. to 70° C. for a predetermined time.

11. The composition of claim 1, wherein the apoptotic mesenchymal stem cell is obtained by heating a stem cell at a temperature in the range of 40° C. to 70° C. for a time period in the range of 1 minute to 1,000 minutes.

12. The composition of claim 1, wherein the apoptotic mesenchymal stem cell is obtained by heating a stem cell at a temperature in the range of 40° C. to 70° C. for a time period in the range of 10 minute to 100 minutes.

13. The composition of claim 1, wherein the apoptotic mesenchymal stem cell is obtained by treating a stem cell with staurosporine in an amount in the range of 1 nm staurosporine to 10,000 nM staurosporine for a time period in the range 1 hour to 1,000 hours.

14. The composition of claim 1, wherein the apoptotic mesenchymal stem cell is obtained by treating a stem cell with staurosporine in an amount in the range of 1 nm staurosporine to 10,000 nM staurosporine for a time period in the range 5 hours to 100 hours.

15. The composition of claim 1, wherein the apoptotic mesenchymal stem cell is obtained by treating a stem cell with staurosporine in an amount in the range of 100 nm staurosporine to 1,000 nM staurosporine for a time period in the range 1 hour to 1,000 hours.

16. The composition of claim 1, wherein the apoptotic mesenchymal stem cell is obtained by treating a stem cell with staurosporine in an amount in the range of 100 nm staurosporine to 1,000 nM staurosporine for a time period in the range 5 hours to 100 hours.

17. The composition of claim 1, wherein the apoptotic mesenchymal stem cell is obtained by treating a stem cell in a serum free medium with staurosporine in an amount in the range of 1 nm staurosporine to 10,000 nM staurosporine for a time period in the range of 1 hour to 1,000 hours.

18. The composition of claim 1, wherein the apoptotic mesenchymal stem cell is obtained by treating a stem cell in a serum free medium with staurosporine in an amount in the range of 1 nm staurosporine to 10,000 nM staurosporine for a time period in the range of 5 hours to 100 hours.

19. The composition of claim 1, wherein the apoptotic mesenchymal stem cell is obtained by treating a stem cell in a serum free medium with staurosporine in an amount in the range of 100 nm staurosporine to 1,000 nM staurosporine for a time period in the range of 1 hour to 1,000 hours.

20. The composition of claim 1, wherein the apoptotic mesenchymal stem cell is obtained by treating a stem cell in a serum free medium with staurosporine in an amount in the range of 100 nm staurosporine to 1,000 nM staurosporine for a time period in the range of 5 hours to 100 hours.

21. The composition of claim 1, wherein the apoptotic mesenchymal stem cell is obtained by irradiating a stem cell at a wavelength in the range of 100 nm to 400 nm for a time period in the range of 0.1 minute to 1,000 minutes.

22. The composition of claim 1, wherein the apoptotic mesenchymal stem cell is obtained by irradiating a stem cell at a wavelength in range of 100 nm to 400 nm for a UV lamp for a time period in the range of 1 minute to 100 minutes.

23. A method for improving:
  (a) colony formation of bone marrow mesenchymal stem cells in vivo and/or in vitro;
  (b) immunomodulation of bone marrow mesenchymal stem cells in vivo and/or in vitro;
  (c) osteogenesis of bone marrow mesenchymal stem cells in vivo and/or in vitro;
  (d) adipogenesis of bone marrow mesenchymal stem cells in vivo and/or in vitro; or
  (e) a combination of (a) to (d),
  comprising contacting the bone marrow mesenchymal cells with the composition of claim 1.

24. A method of claim 23, wherein the method improves the colony formation of bone marrow mesenchymal stem cells in vivo and/or in vitro.

25. A method of claim 23, wherein the method improves the immunomodulation of bone marrow mesenchymal stem cells in vivo and/or in vitro.

26. A method of claim 23, wherein the method improves the osteogenesis of bone marrow mesenchymal stem cells in vivo and/or in vitro.

27. A method of claim 23, wherein the method improves the adipogenesis of bone marrow mesenchymal stem cells in vivo and/or in vitro.

28. A formulation comprising bone marrow-derived mesenchymal stem cells (BMMSC) and the composition of claim 1.

* * * * *

UNITED STATES PATENT AND TRADEMARK OFFICE
CERTIFICATE OF CORRECTION

PATENT NO. : 10,646,518 B2  
APPLICATION NO. : 15/500726  
DATED : May 12, 2020  
INVENTOR(S) : Songtao Shi et al.

Page 1 of 1

It is certified that error appears in the above-identified patent and that said Letters Patent is hereby corrected as shown below:

On the Title Page

On Page 2, Column 2, Item (56), Line 4, under Other Publications, delete "inflamation" and insert --inflammation--.

On Page 2, Column 2, Item (56), Line 35, under Other Publications, delete "Vsascular" and insert --Vascular--.

In the Drawings

Figure 13A:
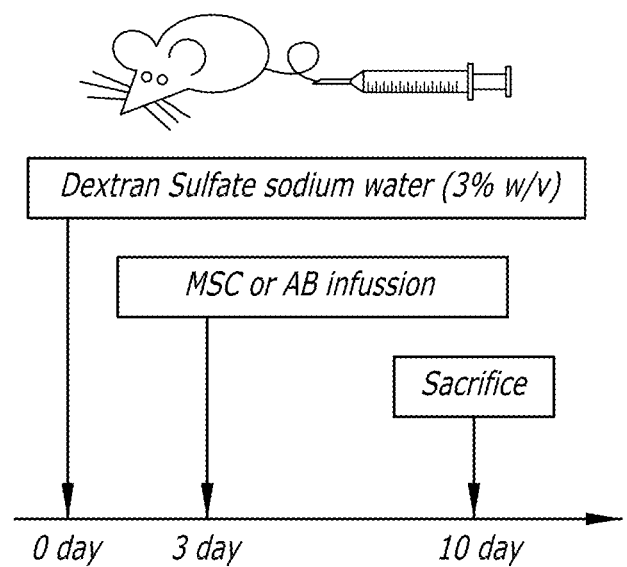
FIGS. 13A-D. Treatment of the colitis mice with apoptotic bodies.
Figure 13B:
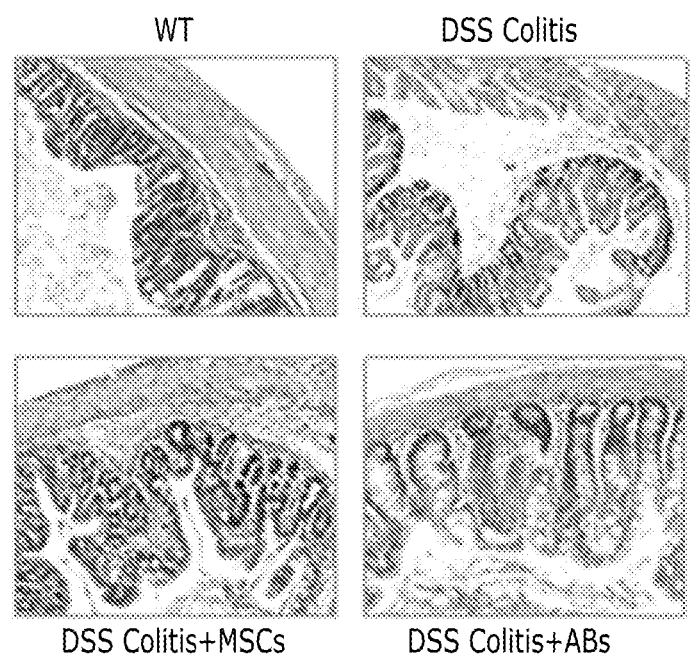
Figure 13C:
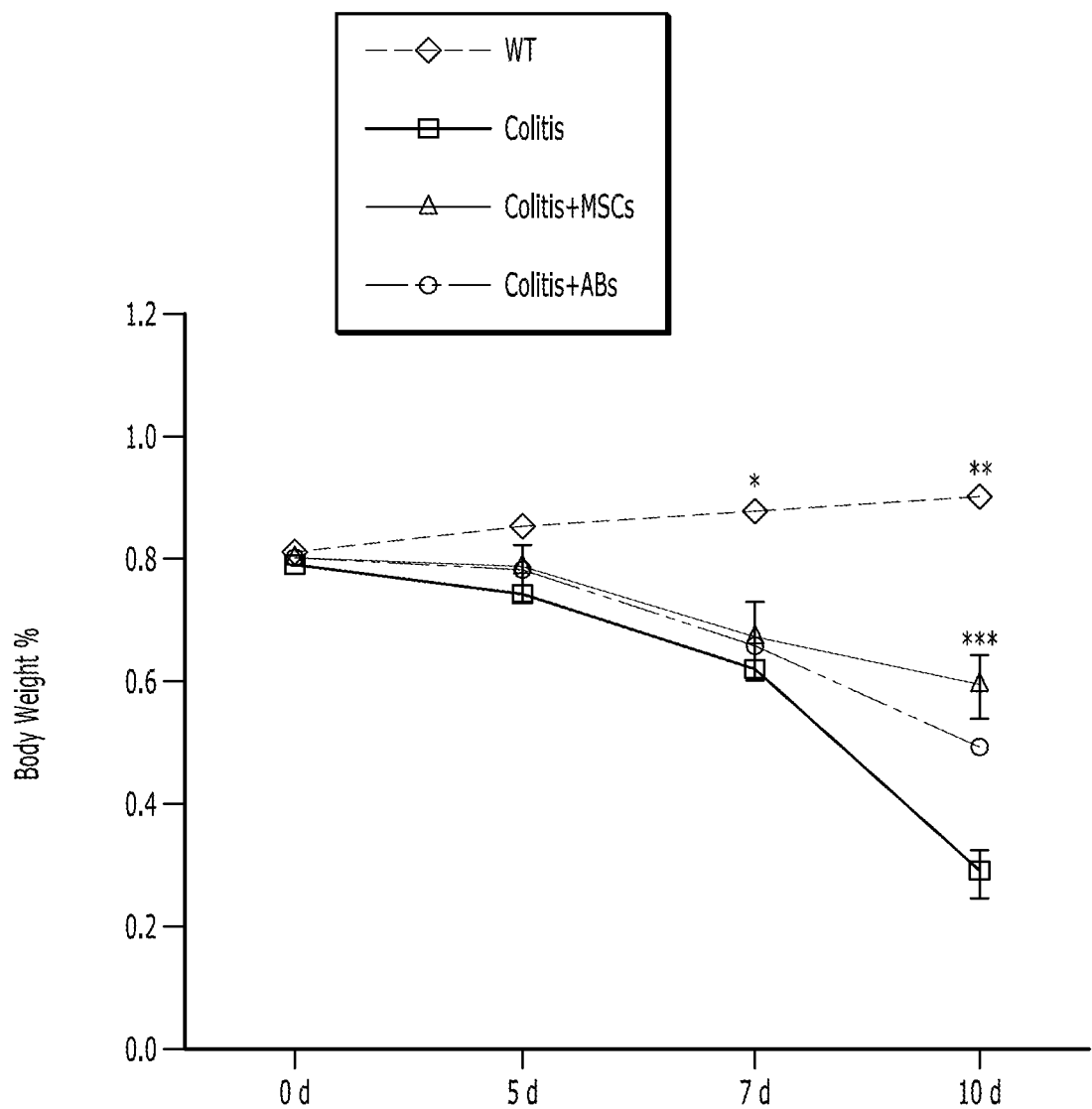
Figure 13D:
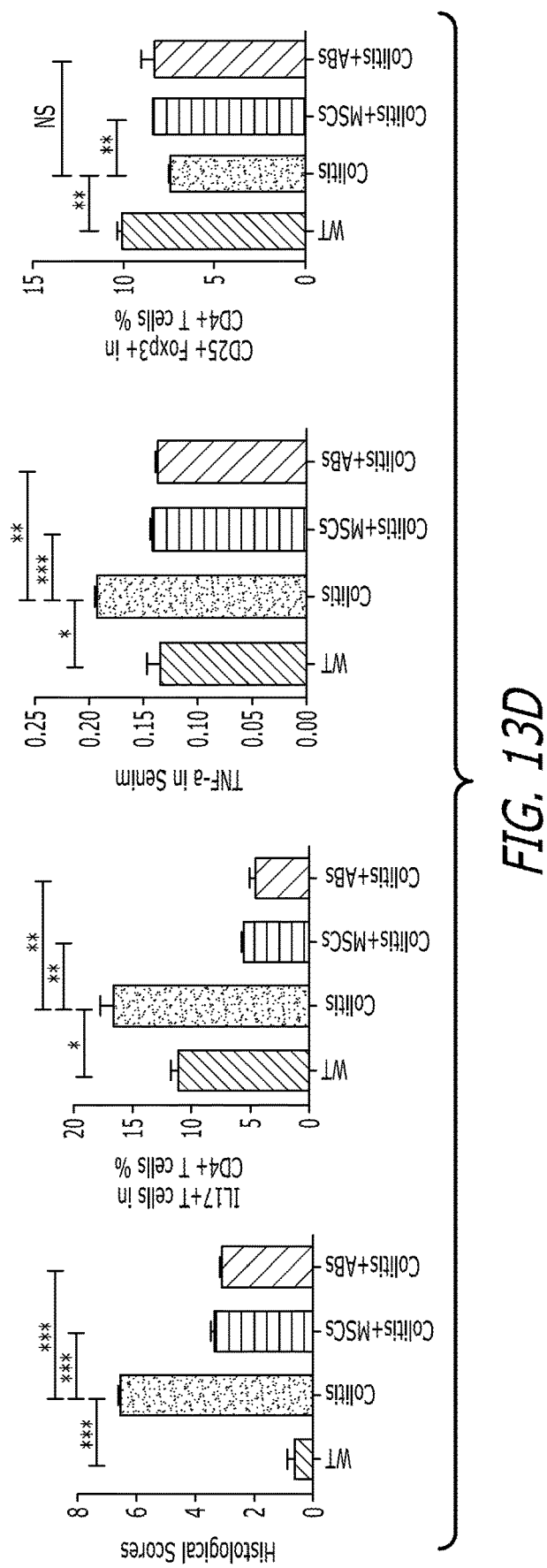

On Sheet 13 of 34, FIG. 13A, Line 2 (Approx.), delete "infussion" and insert --infusion--.

Figure 14A:
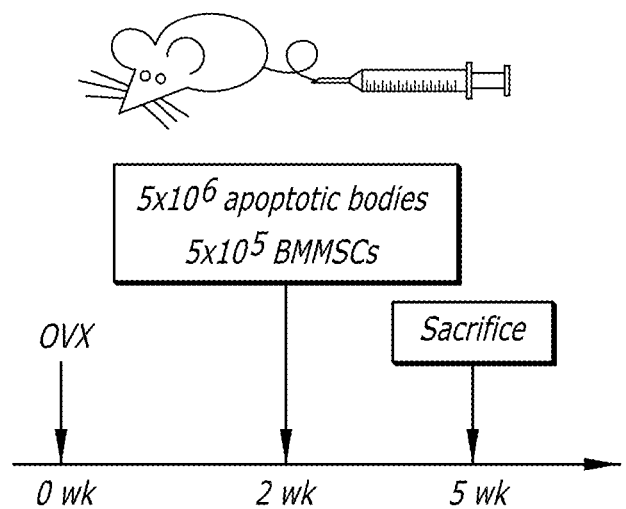
FIGS. 14A-I. Treatment of the ovariectomized mice with apoptotic bodies.
Figure 14B:
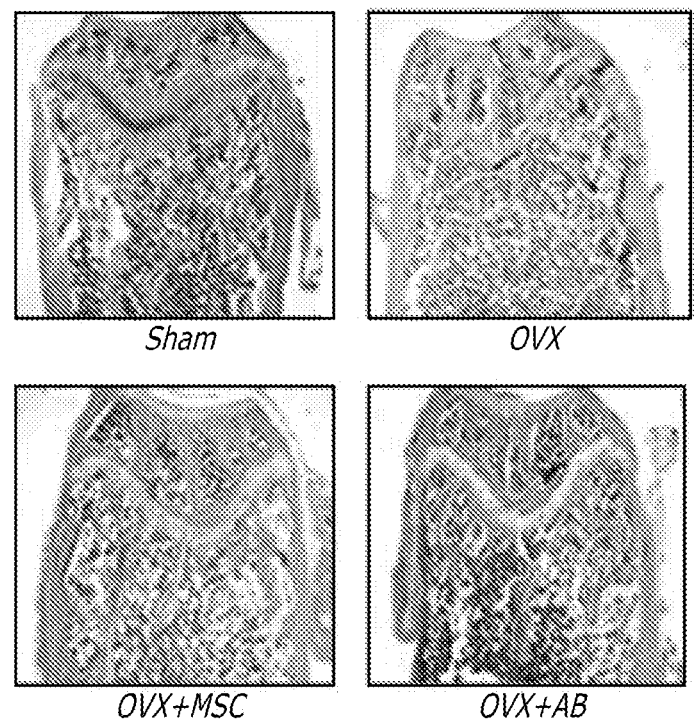
Figure 14C:
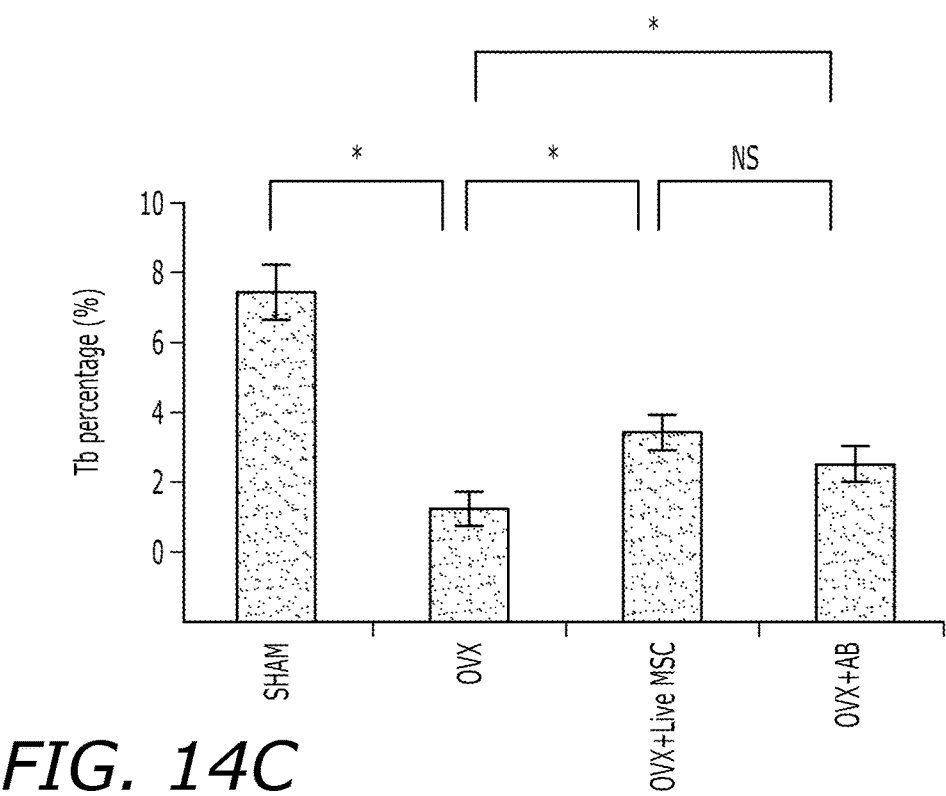
Figure 14D:
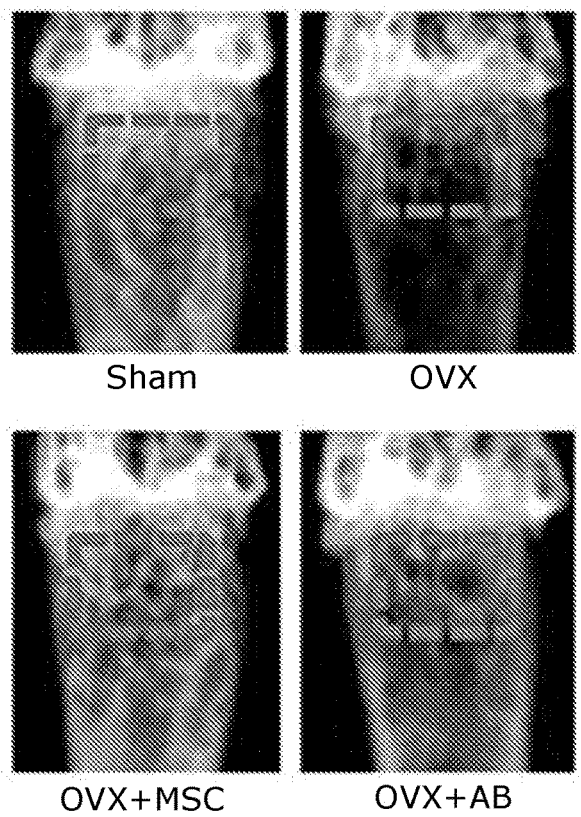
Figure 14E:
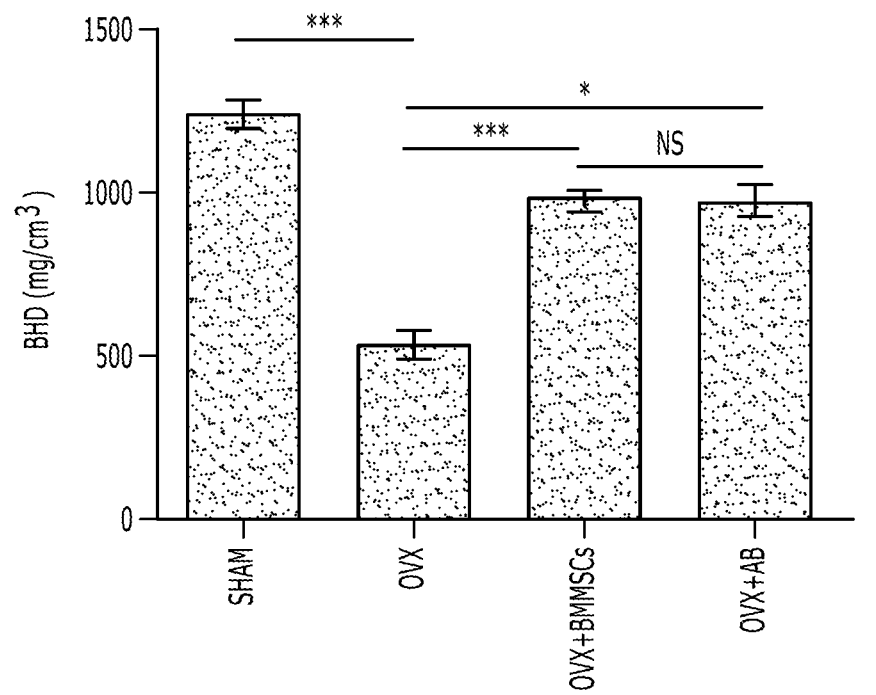
Figure 14E:
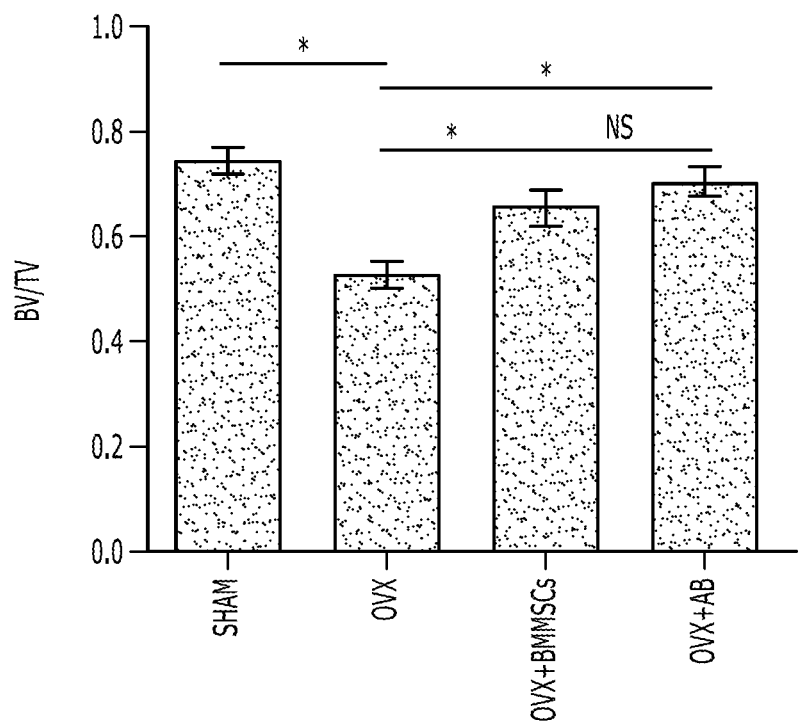
Figure 14F:
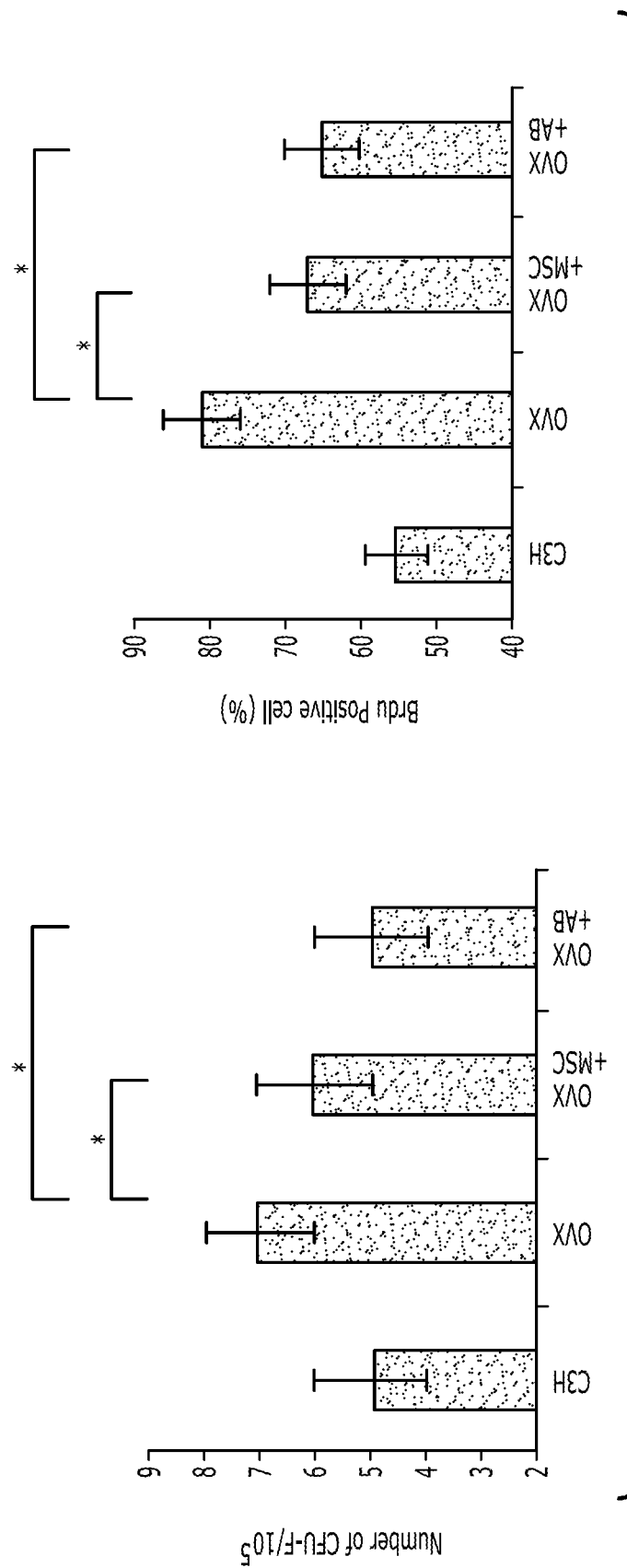
Figure 14G:
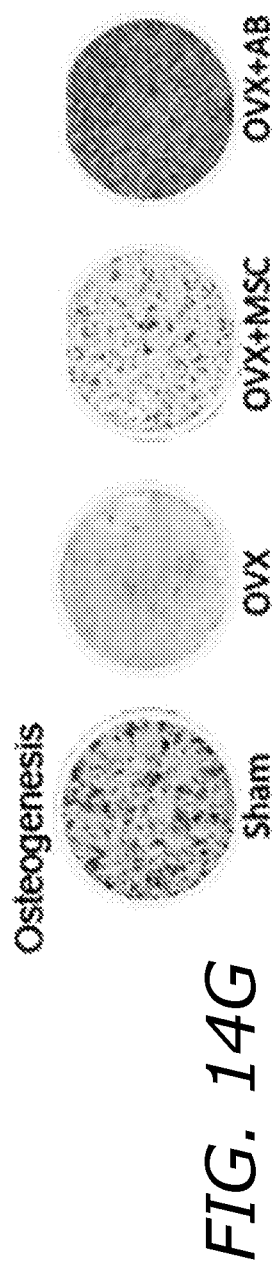
Figure 14H:
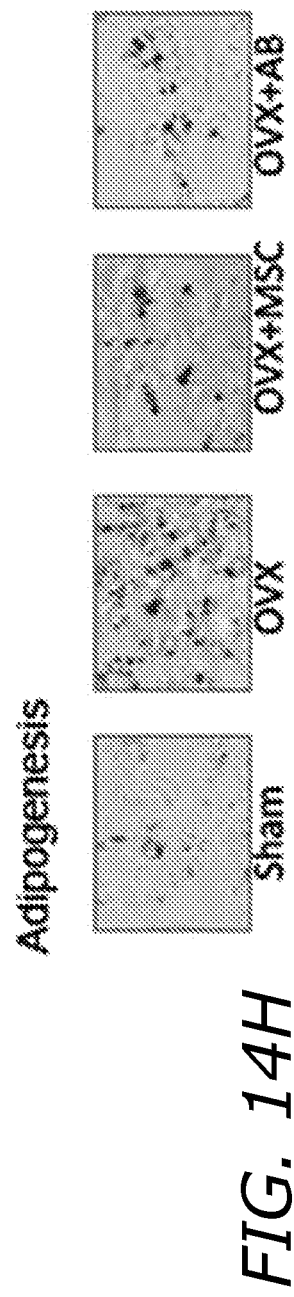
Figure 14I:
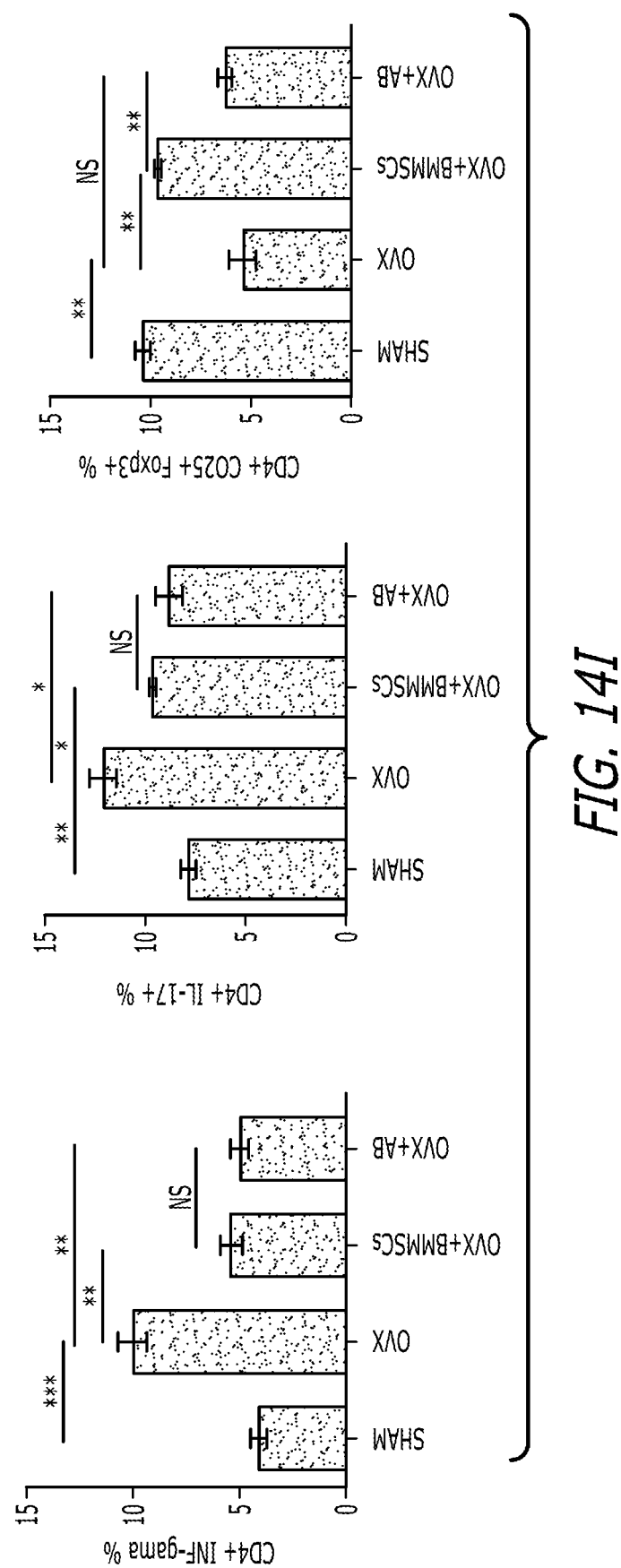
Figure 15A:
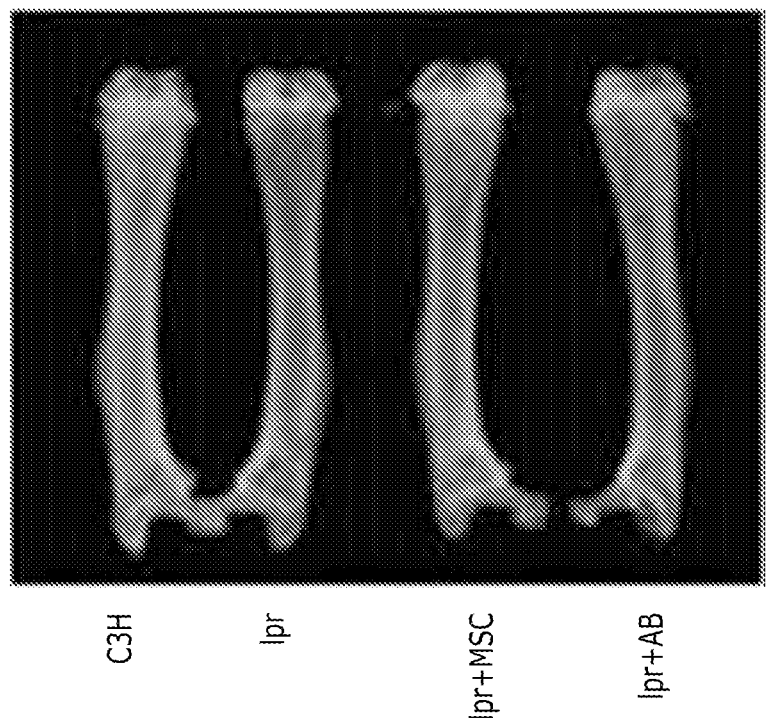
Figure 15B:
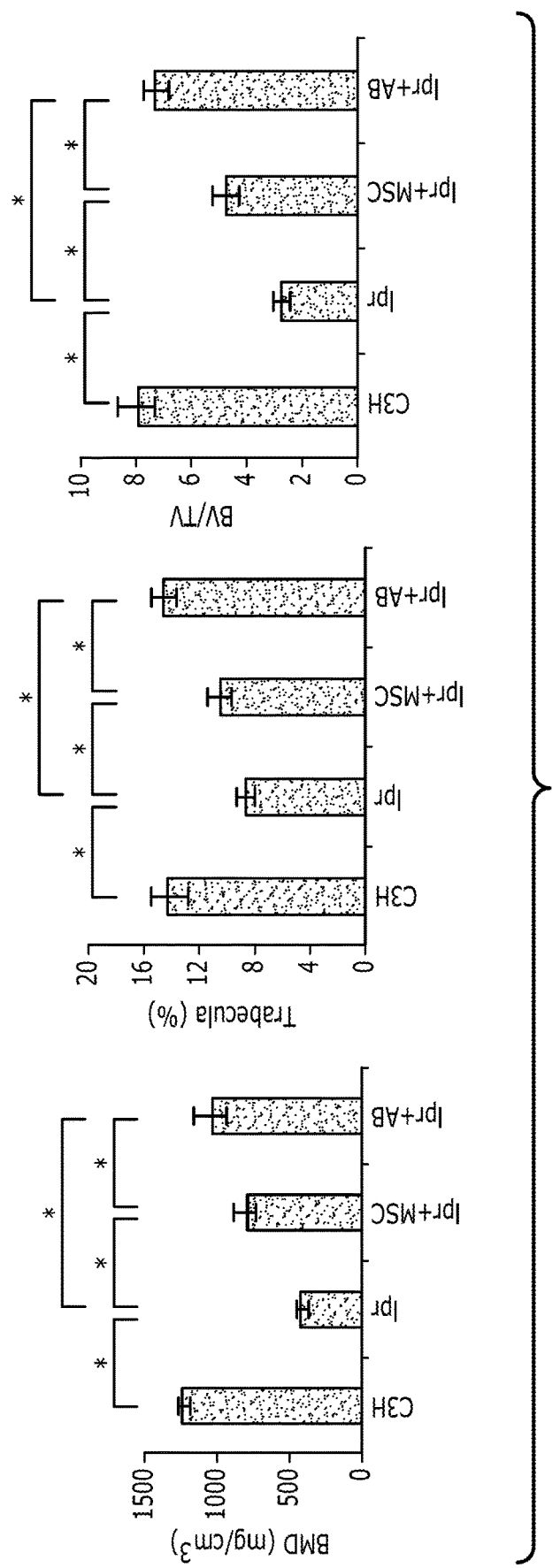
Figure 15C:
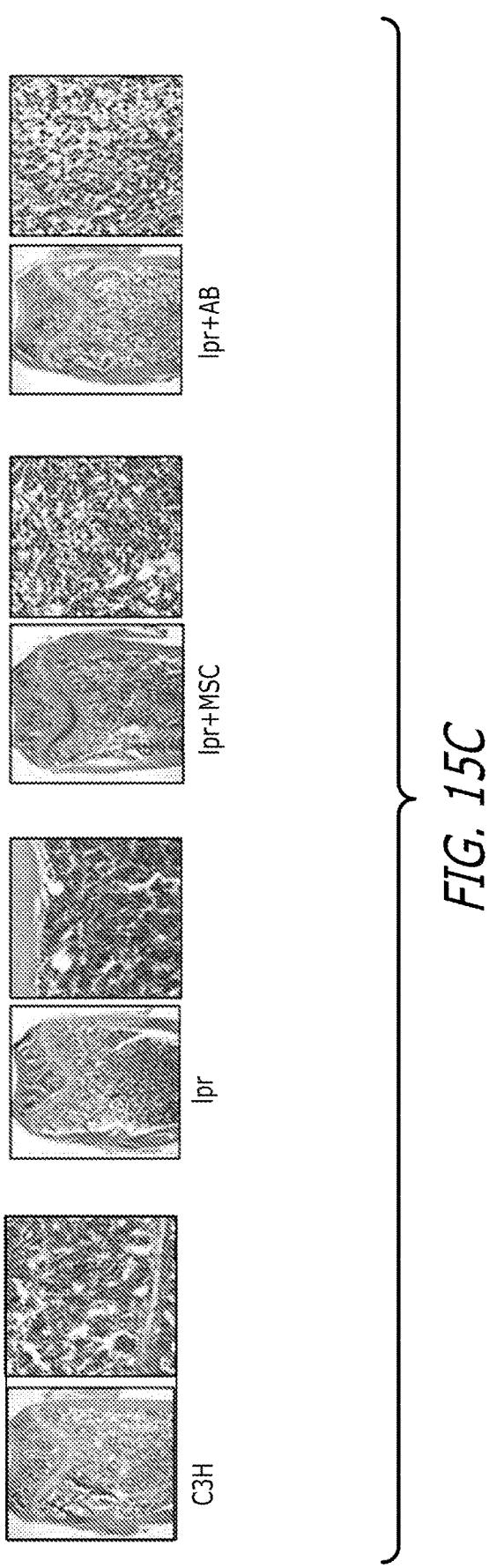
Figure 15D:
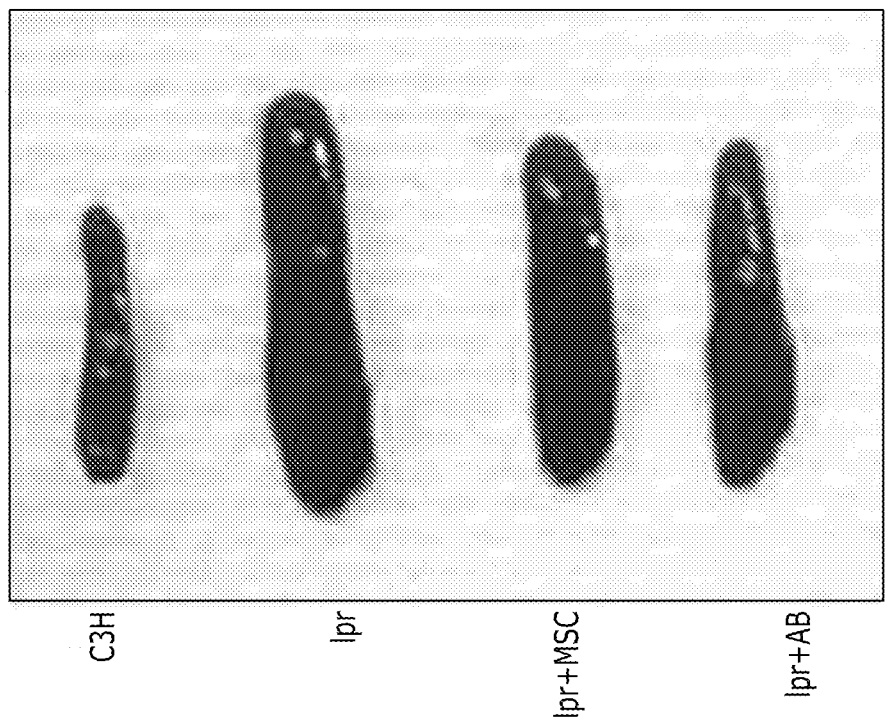
Figure 15E:
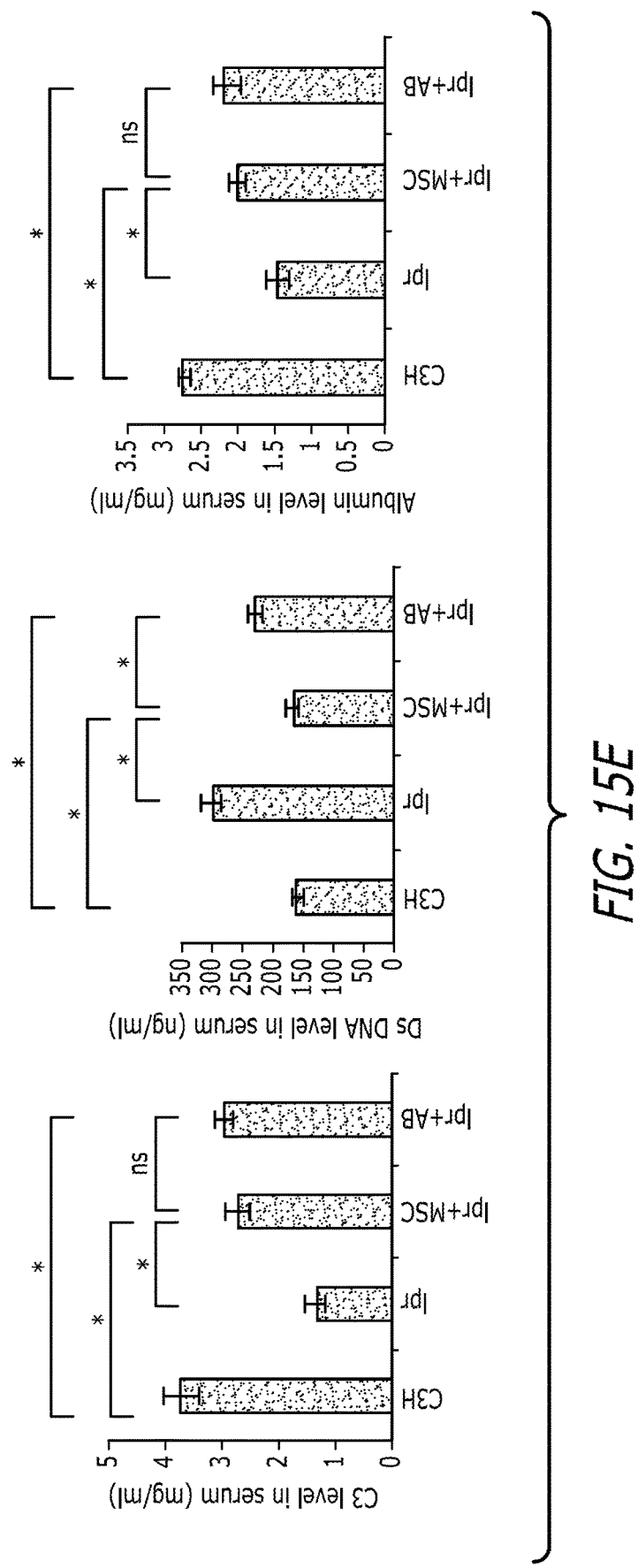

On Sheet 21 of 34, FIG. 14I, Y-axis, delete "gama" and insert --gamma--.

In the Specification

In Column 7, Line 13, delete "to to" and insert --to--.

In Column 9, Line 25, delete "p 151" and insert --p151--.

In Column 10, Line 65, delete "(of" and insert --of--.

In Column 11, Line 23, delete "metastisis" and insert --metastasis--.

In Column 16, Line 67, delete "hepatocelluar" and insert --hepatocellular--.

In Column 17, Line 8, delete "Isocove's" and insert --Iscove's--.

In Column 17, Lines 36-37, delete "Hematoxyin" and insert --Hematoxylin--.

Signed and Sealed this  
Twenty-fifth Day of August, 2020

Andrei Iancu  
*Director of the United States Patent and Trademark Office*